(12) United States Patent
Kimura et al.

(10) Patent No.: US 9,326,979 B2
(45) Date of Patent: May 3, 2016

(54) MEDICINAL COMPOSITION FOR TRANSDERMAL ABSORPTION, MEDICINAL COMPOSITION STORING UNIT AND TRANSDERMAL ABSORPTION PREPARATION USING THE SAME

(75) Inventors: Takahito Kimura, Toyama (JP); Masahiro Orihashi, Toyama (JP); Shigeto Fujishita, Toyama (JP); Koichi Takabatake, Toyama (JP); Tatsuhisa Kato, Toyama (JP); Satoshi Shiota, Toyama (JP); Yuichiro Shima, Toyama (JP)

(73) Assignee: TEIKA PHARMACEUTICAL CO., LTD., Toyama-shi (JP)

( * ) Notice: Subject to any disclaimer, the term of this patent is extended or adjusted under 35 U.S.C. 154(b) by 635 days.

(21) Appl. No.: 12/529,191

(22) PCT Filed: Feb. 29, 2008

(86) PCT No.: PCT/JP2008/053597
§ 371 (c)(1),
(2), (4) Date: Aug. 31, 2009

(87) PCT Pub. No.: WO2008/108286
PCT Pub. Date: Sep. 12, 2008

(65) Prior Publication Data
US 2010/0074943 A1 Mar. 25, 2010

(30) Foreign Application Priority Data
Mar. 2, 2007 (JP) ................................. 2007-053102

(51) Int. Cl.
| | | |
|---|---|---|
| A61K 31/485 | (2006.01) |
| A61K 9/70 | (2006.01) |
| A61K 47/10 | (2006.01) |
| A61K 47/12 | (2006.01) |
| A61K 47/28 | (2006.01) |
| A61K 9/00 | (2006.01) |
| A61K 9/10 | (2006.01) |

(52) U.S. Cl.
CPC ............. *A61K 31/485* (2013.01); *A61K 9/0014* (2013.01); *A61K 9/10* (2013.01); *A61K 9/7084* (2013.01); *A61K 47/10* (2013.01); *A61K 47/12* (2013.01); *A61K 47/28* (2013.01)

(58) Field of Classification Search
None
See application file for complete search history.

(56) References Cited

U.S. PATENT DOCUMENTS

| | | | |
|---|---|---|---|
| 4,719,226 A * | 1/1988 | Otsuka et al. ................. | 514/449 |
| 4,855,294 A | 8/1989 | Patel et al. | |
| 5,503,844 A * | 4/1996 | Kwiatek et al. ............... | 424/449 |
| 2004/0191301 A1 | 9/2004 | Van Duren | |

FOREIGN PATENT DOCUMENTS

| | | | |
|---|---|---|---|
| EP | 748629 A1 * | 12/1996 | |
| EP | 0 900 076 | 3/1999 | |
| JP | 06048962 A * | 2/1994 | |
| JP | 6-199668 | 7/1994 | |
| JP | 7-33681 | 2/1995 | |
| JP | 7-300418 | 11/1995 | |
| JP | 8-143458 | 6/1996 | |
| JP | 2669951 | 7/1997 | |
| JP | 2775053 | 5/1998 | |
| JP | 2843923 | 10/1998 | |
| JP | 2000-507241 A | 6/2000 | |
| JP | 2001-39865 A | 2/2001 | |
| JP | 2001-151668 A | 6/2001 | |
| JP | 3280711 | 2/2002 | |
| JP | 2003-501446 A | 1/2003 | |
| JP | 3493434 | 11/2003 | |
| JP | 3514480 | 1/2004 | |
| JP | 2005-537299 A | 12/2005 | |
| JP | 2005-537299 A5 | 12/2005 | |
| JP | 2006-45158 A | 2/2006 | |
| JP | 2006-248996 A | 9/2006 | |

(Continued)

OTHER PUBLICATIONS

CAS Registry No. 57-27-2 (Nov. 16, 1984).*

(Continued)

*Primary Examiner* — Bethany Barham
*Assistant Examiner* — Peter Anthopolos
(74) *Attorney, Agent, or Firm* — Oblon, McClelland, Maier & Neustadt, L.L.P.

(57) ABSTRACT

An object of the invention is to provide a transdermal absorption preparation capable of sustaining the blood morphine concentration at an effective level over at least 48 hours, etc. This transdermal absorption preparation comprises a medicinal composition for transdermal absorption in which an active ingredient selected from morphine and salts thereof is blended in such an amount as corresponding to the saturation solubility or more in an active ingredient-holding vehicle having fluidity at a temperature around the human skin surface temperature and at least a portion of the active ingredient is held in a crystalline form, characterized in that, in the case where a preparation obtained from the above-described medicinal composition for transdermal absorption is applied to the uninjured skin of the back of a white rabbit having been shaven with electrical clippers for 72 hours, the available amount of the active ingredient per single dose of the preparation is from 10 mg to 400 mg in terms of morphine base, and the plasma concentrations of the active ingredient 24 hours and 48 hours after the application of the preparation under the above-described conditions are each at least 40 ng/mL in terms of morphine base, and so on.

31 Claims, 2 Drawing Sheets

(56) References Cited

FOREIGN PATENT DOCUMENTS

| WO | WO 92/08459 | 5/1992 |
| WO | 95 24197 | 9/1995 |
| WO | WO 97/34587 | 9/1997 |
| WO | WO 99/14283 | 3/1999 |
| WO | WO 00/06659 | 2/2000 |
| WO | WO 00/76314 A1 | 12/2000 |
| WO | WO 2004/014432 A1 | 2/2004 |
| WO | WO 2006047362 A2 * | 5/2006 |

OTHER PUBLICATIONS

CAS Registry No. 52-26-6 (Nov. 16, 1984).*
Yutaka Tsutsumi, et al., "Withdrawal Symptoms from Transdermal Fentanyl (TDF) after an Allogeneic Peripheral Blood Stem Cell Transplant (PBSCT)", Pain Medicine, vol. 7, No. 2, Mar.-Apr. 2006, pp. 164-165.
Extended European Search Report issued Apr. 24, 2013, in corresponding European patent application No. EP 08721045.
https://www.jstage.jst.go.jp/article/dds/22/4/22_4_450/_pdf, p. 451, Table 1, (2007) (partial English-language translation).
4 Myths About Transdermal Drug Delivery, Issue Date: vol. 3, No. 4, Jun. 2003. http://samkeller.com/ME2/dirmod.asp?sid=&nm=&type=Publishing&mod=Publications%3A%3AArticle&mid=8F3A7027421841978F18BE895F87F791&tier=4&id=5AA8C8DA257F4A36963672D016FB4396.
Drug Bank: Morphine (DB00295). http://www.drugbank.ca/drugs/DB00295. (Created Jun. 13, 2005, updated Jul. 15, 2013).
Excerpt from Merck Index, 12th ed. Merck: Whitehouse Station, NJ, 1996 (Merck Index).
Roy, et al., Pharmaceutical Research, vol. 6, No. 10, 1989.
Westerling, et al., Br J clin Pharmac 1994, 37.
Margetts, et al., Continuing Education in Anesthesia, Critical Care & Pain, vol. 7, No. 5, 2007.
Banga, Electrically Assisted Transdermal and Topical Drug Delivery, CRC Press, Sep. 26, 2002 (https://books.google.co.jp/books?id=wKHjtndRSDMC&pg=PA30).

* cited by examiner

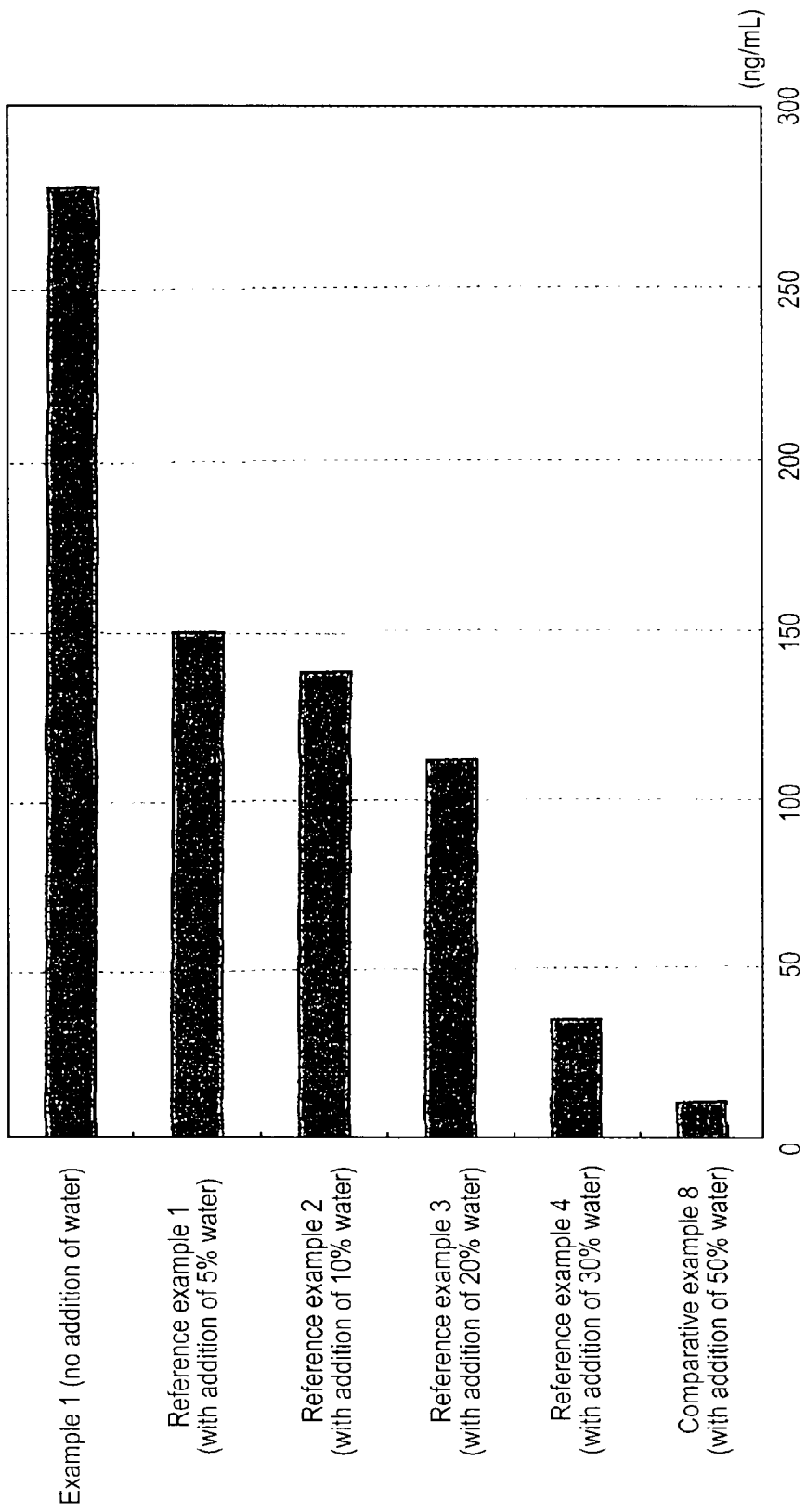

MEDICINAL COMPOSITION FOR TRANSDERMAL ABSORPTION, MEDICINAL COMPOSITION STORING UNIT AND TRANSDERMAL ABSORPTION PREPARATION USING THE SAME

TECHNICAL FIELD

The present invention relates to a medicinal composition for transdermal absorption, a medicinal composition storing unit and a transdermal absorption preparation using the same, and more particularly it relates to a pharmaceutical medicinal composition for transdermal absorption, a medicinal composition storing unit and a transdermal absorption preparation capable of providing sustained transdermal administration of morphine or a salt thereof.

BACKGROUND ART

Narcotics typified by morphine (chemical name: 7,8-didehydro-4,5α-epoxy-17-methylmorphinan-3,6α-diol) or a salt thereof have been clinically used for the purpose of easing postoperative pain or cancer pain since a long time ago. Recently, improvement of patients' QOL has become of importance and pain palliative medicine (palliative care) has been promoted, leading to significant increase in the used amount of narcotics.

In "Cancer Pain Relief" published by the World Health Organization in 1986, the following five points are listed as five basic rules in cancer pain treatment:
(1) by the mouth;
(2) by the clock;
(3) by the ladder;
(4) for the individual; and
(5) with attention to detail.

The reason why "(1) by the mouth" is stated is that, at the time of publication, oral administration was the most excellent in terms of patients' QOL among the administration methods of analgesics. As for other administration methods, for example, rectal administration has problems in that it is difficult to carry out the method for patients with diarrhea, melena or stoma, and also it is difficult to give a large dose. In addition, although sustained subcutaneous infusion or sustained intravenous infusion has an advantage in that the infusion rate is easy to control, the activity of patients is restricted and therefore, QOL is remarkably poor. Accordingly, oral administration is commonly used as the first choice.

In actuality, however, it often becomes difficult for cancer patients particularly in the end stages to orally take a drug, and there is no other choice but to choose rectal administration, sustained subcutaneous infusion or sustained intravenous infusion which is inferior from the viewpoint of the above-mentioned QOL. Therefore, a novel administration route capable of providing better QOL to patients has been explored.

As means for solving this problem, there is a transdermal therapeutic system (TTS) for systemically administering a drug through the skin. This TTS has a lot of advantages as compared with oral administration in that (1) the blood concentration can be maintained constant over a long period of time; (2) a first-pass effect in the liver can be avoided; (3) side effects on the gastrointestinal tract can be reduced; (4) administration to patients with difficulty in swallowing such as small children or elder people can be performed; (5) even in the case where side effects are developed, administration can be easily discontinued by detaching the system, and the like. Therefore, the development of the system has been actively carried out recently.

In Japan, a sustained transdermal absorption therapeutic agent for cancer pain containing fentanyl (trade name "Durotep Patch") placed on the market in 2001 is a product that solves the above problem to a certain degree by employing this TTS.

Fentanyl generally has an advantage of having less side effects such as constipation, nausea or dizziness than morphine or a salt thereof, and, this is considered to be attributable to the fact that morphine or a salt thereof has a different mechanism of action from that of fentanyl. Specifically, the drugs are both µ receptor agonists, but µ receptor is classified into two subtypes in mice: µ1 receptor involved in expression of physical dependence such as leaps and shudders; and µ2 receptor involved in expression of physical dependence such as diarrhea and body weight loss and mental dependence. It is known that fentanyl has a relatively higher selectivity for the µ1 receptor than morphine and the pharmacological action of fentanyl via the µ2 receptor is considered to be weak also in humans. Accordingly, this does not eliminate the need for morphine.

Further, although the number of such cases is relatively few, cases have been reported in which symptoms considered to be withdrawal symptoms caused by physical dependence of morphine were developed when a drug was changed from morphine or a salt thereof to fentanyl (Non-patent document 1). This is one of the reasons why doctors hesitate about switching to fentanyl. As described above, fentanyl cannot serve as a complete alternative drug to morphine.

Accordingly, if there is a preparation with which transdermally administering an effective amount of morphine or a salt thereof in a sustained manner becomes capable, the above-mentioned problems are all solved, and thus, such a preparation has been demanded. However, morphine or a salt thereof is a drug having a property of extremely low skin permeability, and therefore, the development of such a preparation was very difficult.

An attempt to formulate morphine or a salt thereof or a substance related thereto into a transdermal or transmucosal absorption preparation has been made since a long time ago. For example, techniques as described below have been known.

That is, a method for transnasal delivery of morphine gluconate is disclosed in Patent document 1; a transdermal absorption accelerator selected from terpenes and essential oils, a transdermal absorption accelerator aid comprising a lower alcohol and water or a lower glycol, and an aqueous or lower glycol-based transdermal absorption composition containing a salt of morphine are disclosed in Patent document 2; and a composition obtained by blending a narcotic analgesic in a base containing a lower alcohol, a polar solvent and an azacyclo alkane derivative is disclosed in Patent document 3.

Further, an external preparation of a morphine-type compound with the addition of a medium-chain fatty acid monoglyceride in an amount of from 50 to 99.95% by weight of the total weight of the preparation is disclosed in Patent document 4; a local composition for transdermal delivery of a prodrug derivative of morphine is disclosed in Patent document 5; a transdermal absorption preparation comprising a support and, laminated thereon, an adhesive, a transdermal absorption accelerator selected from the group consisting of hydroxycarboxylic acids and dicarboxylic acids having 2 to 8 carbon atoms and a base containing crospovidone and morphine hydrochloride or morphine sulfate is disclosed in Patent document 6; an ointment containing a morphine, a medium-chain fatty acid monoglyceride and a long-chain saturated fatty acid glyceride is disclosed in Patent document 7; and a transdermal device suitable for continuous administration of an opiate/opioid analgesic over a period of about 24 to 144 hours via a region of the skin from which the epidermis has been removed is disclosed in Patent document 8.

Further, a transdermal absorption patch comprising a support and, provided thereon, an adhesive layer containing an adhesive, an acid addition salt of morphine and a transdermal absorption accelerator, wherein the transdermal absorption accelerator is (A) a compound having a log P value (P denotes a partition coefficient in an octanol-water system) of from −0.5 to 2.0, (B) an oxycarboxylic acid having 2 to 8 carbon atoms and/or a dicarboxylic acid having 2 to 8 carbon atoms, and (C) a compound selected from the group consisting of fatty acid amides which are reaction products of an aliphatic monocarboxylic acid having 10 to 14 carbon atoms with a mono- or diethanolamine, acyl sarcosines and alkyl hydroxybenzoates having an alkyl group with 1 to 5 carbon atoms is disclosed in Patent document 9; and a transdermal absorption patch comprising a support and, provided on one surface thereof, an adhesive layer containing an adhesive, a drug, an adhesion-imparting agent and a transdermal absorption accelerator, wherein the drug is an acid addition salt of morphine, and the adhesion-imparting agent is a hydrogenated rosin glycerin ester, and the transdermal absorption accelerator contains (A) an organic compound having a log P value (P denotes a partition coefficient in an octanol-water system) of from −0.5 to 2.0, and/or (B) an oxycarboxylic acid having 2 to 8 carbon atoms and/or a dicarboxylic acid having 2 to 8 carbon atoms is disclosed in Patent document 10.

Further, an aqueous transdermal absorption preparation characterized by incorporating morphine hydrochloride uniformly in a base microemulsion containing a monoester or a diester composed of propylene glycol and a medium-chain fatty acid, a medium-chain fatty acid monoglyceride, a surfactant and water is disclosed in Patent document 11; a patch obtained by blending morphine, an acrylic adhesive and triacetin is disclosed in Patent document 12; and an ointment containing morphine and an effective amount of one of or a complex of two or more of phosphate derivatives of a lipophilic and pharmaceutically acceptable compound is disclosed in Patent document 13.

However, all these have problems in that (1) the blood concentration of the active ingredient or the skin permeation rate of the active ingredient obtained in the experiment is low and when the data is extrapolated to humans, the probability that the blood concentration does not reach an effective blood concentration is high; (2) a ratio of the applied area to the body surface area in the experiment is significantly high and when the data is extrapolated to humans, the probability that the size exceeds a practically applicable preparation size is high; (3) the duration of action is extremely short (less than 24 hours), and the like, and are not satisfactory as means for solving the above-mentioned problems, and practically, there has been no preparation capable of transdermally administering morphine or a salt thereof in a sustained manner in the market.

Patent document 1: JP-T-2003-501446
Patent document 2: Japanese Patent No. 2669951
Patent document 3: Japanese Patent No. 2843923
Patent document 4: Japanese Patent No. 2775053
Patent document 5: Japanese Patent No. 3493434
Patent document 6: Japanese Patent No. 3280711
Patent document 7: Japanese Patent No. 3514480
Patent document 8: JP-T-2000-507241
Patent document 9: JP-A-H07-300418
Patent document 10: JP-A-H08-143458
Patent document 11: JP-A-2001-151668
Patent document 12: JP-A-2001-039865
Patent document 13: JP-T-2005-537299
Non-patent document 1: Pain Med. 2006 March-April; 7(2):164-5

DISCLOSURE OF THE INVENTION

Problems that the Invention is to Solve

The present invention has been made in view of the above circumstances and has its object to provide a medicinal composition for transdermal absorption capable of sustaining the blood concentration of morphine at an effective level over at least 48 hours when it is applied to humans.

Further, the invention has its object to provide a medicinal composition storing unit for storing the composition and a transdermal absorption preparation using the medicinal composition storing unit.

Means for Solving the Problems

The present inventors made intensive studies on transdermal absorption preparations containing morphine or a salt thereof as an active ingredient, and as a result, they found that by blending morphine or a salt thereof in a specific active ingredient-holding vehicle under given conditions, morphine can be released over a long period of time, and thus the invention has been completed.

That is, the invention is directed to a medicinal composition for transdermal absorption in which an active ingredient selected from morphine and salts thereof is blended in an active ingredient-holding vehicle having fluidity at a temperature around the human skin surface temperature in an amount corresponding to the saturation solubility or more, and at least a portion of the active ingredient is held in a crystalline form, characterized in that, in the case where a preparation obtained from the medicinal composition for transdermal absorption is applied to the uninjured skin of the back of a white rabbit having been shaven with electrical clippers for 72 hours, the available amount of the active ingredient per single dose of the preparation is from 10 mg to 400 mg in terms of morphine base, and the plasma concentrations of the active ingredient 24 hours and 48 hours after the application of the preparation under the above-mentioned conditions are each at least 40 ng/mL in terms of morphine base.

Further, the invention relates to a medicinal composition storing unit comprising a support having voids with which the above-mentioned medicinal composition for transdermal absorption is carried.

Further, the invention relates to a transdermal absorption preparation comprising the above-mentioned medicinal composition storing unit and, sequentially laminated on a surface thereof opposite to the surface to be applied to the skin, an impermeable layer which practically does not allow the active ingredient and the active ingredient-holding vehicle to permeate therethrough, an adhesive layer and an adhesive holding layer.

Still further, the invention relates to a method for relieving pain characterized by applying any of the above-mentioned medicinal composition for transdermal absorption, medicinal composition storing unit and transdermal absorption preparation to a patient with pain.

Effects of the Invention

According to the invention, it becomes possible to provide a sustained-action medicinal composition for transdermal absorption capable of sustaining the blood morphine concentration at a level of clinically effective amount for at least 48 hours when applied to humans.

BEST MODE FOR CARRYING OUT THE INVENTION

Hereinafter, the present invention will be described in further detail.

The active ingredient of the medicinal composition for transdermal absorption of the invention is selected from morphine and salts thereof. As the active ingredient, either morphine or a salt thereof can be used, and particularly preferably, a salt of morphine.

The salt of morphine as used herein is an acid addition compound of morphine which is a base, and specific examples thereof include morphine hydrochloride, morphine sulfate, morphine gluconate, morphine tartrate, morphine lactate, morphine methane sulphonate and morphine phosphate. Among these, morphine hydrochloride and morphine sulfate are preferred from the viewpoints that they have been widely used and a large amount of data regarding safety are accumulated, and they are easily available. Further, if necessary, it is also possible to use one compound or a mixture of two or more compounds of the above-mentioned compounds as the active ingredient.

In the invention, the above-mentioned morphine or a salt thereof (hereinafter sometimes referred to as "active ingredient") is blended in an active ingredient-holding vehicle having fluidity at a temperature around the human skin surface temperature in an amount corresponding to the saturation solubility or more, and at least a portion of the active ingredient is held in a crystalline form. The active ingredient-holding vehicle as used herein is one substance or a mixture of two or more substances having a solubility to such an extent that, when the active ingredient is blended therein in a prescribed amount, at least a portion of the active ingredient can be held in a crystalline form, and having fluidity at a temperature around the human skin surface temperature.

By using such an active ingredient-holding vehicle, the active ingredient is blended in the active ingredient-holding vehicle in an amount corresponding to the saturation solubility or more, and at least a portion of the active ingredient is held in a crystalline form.

In the invention, the function of the above-mentioned active ingredient-holding vehicle has not necessarily been elucidated; however, it is presumed that the active ingredient-holding vehicle plays a role as a carrier that carries the active ingredient, which is held in a crystalline form and present in a place where the active ingredient is not directly in contact with the skin, and a transdermal absorption accelerator to the skin surface. Therefore, it is necessary that the active ingredient-holding vehicle have adequate fluidity to such an extent that the above object is achieved under actual application conditions.

On the other hand, when the active ingredient-holding vehicle does not have fluidity, in other words, when the active ingredient-holding vehicle is such a substance that has shape retainability by itself, it does not play a role as a carrier and as a result, the availability of the active ingredient is decreased. Therefore, such active ingredient-holding vehicle is not preferred. However, even if the active ingredient-holding vehicle is a substance having low shape retainability by itself, it can be used without any problem as long as it is such a substance that, when any of the medicinal composition for transdermal absorption, the medicinal composition storing unit and the percutaneous absorption preparation is actually applied to humans, can be sufficiently blended or made to flow by the movement of patients or the convection in the medicinal composition storing unit due to a difference between the skin temperature and the ambient temperature.

As the active ingredient-holding vehicle, any substance can be used as long as it has the above-mentioned property. As an example of the active ingredient-holding vehicle, one substance or a mixture of two or more substances selected from a transdermal absorption accelerator, a skin irritation reducing agent, a stabilizing agent, a pH adjusting agent, a viscosity controlling agent, a crosslinking agent, an antioxidant, a preservative, an emulsifying agent, an antiseptic, a solubilizing agent and the like can be given. Specifically, one substance or a mixture of two or more substances selected from a substance including a mixture of hydrocarbons as a main component, a glycol, a polyether, a silicone oil, an intercellular lipid component, a long-chain fatty acid alkyl ester, a saturated higher fatty acid, an unsaturated higher fatty acid, a higher alcohol, an alkylene oxide adduct of a higher alcohol, a crotonotoluidine derivative, hydroxy acid and water can be given. More specifically, one or more substances selected from liquid paraffin, propylene glycol, 1,3-butylene glycol, polyethylene glycol, polyvinylpyrrolidone, a silicone oil, ceramide, cholesterol, isopropyl palmitate, lauric acid, palmitic acid, oleic acid, oleyl alcohol, polyoxyethylene lauryl ether, crotamiton, lactic acid, isopropyl myristate, polyoxyethylene hydrogenated castor oil, sorbitan monolaurate and water can be given. Among these, particularly propylene glycol and 1,3-butylene glycol can be advantageously used. Generally, the molecular weight of the polyethylene glycol is preferably 4000 or less, more preferably 1500 or less, further, particularly preferably 1000 or less from the viewpoint of the melting point and viscosity thereof.

The "temperature around the human skin surface temperature" as used herein means a possible temperature of the skin to which the medicinal composition for transdermal absorption of the invention, or the below-mentioned medicinal composition storing unit or transdermal absorption preparation is applied under the common conditions of use. It means generally the range from 28° C. to 38° C., more commonly the range from 30° C. to 36° C., and the most commonly the range from 31° C. to 35° C.

The medicinal composition for transdermal absorption (hereinafter sometimes referred to as "medicinal composition") of the invention is produced by blending the above-mentioned active ingredient in the active ingredient-holding vehicle and as needed, the below-mentioned transdermal absorption accelerator or other components according to a common procedure. When a preparation obtained from the composition is applied to the uninjured skin of the back of a white rabbit having been shaven with electrical clippers for 72 hours, the available amount of the active ingredient per single dose of the preparation is from 10 mg to 400 mg in terms of morphine base.

The available amount in terms of morphine base is preferably from 15 mg to 350 mg, more preferably from 20 to 300 mg, particularly preferably from 25 to 250 mg.

If the available amount in terms of morphine base after the medicinal composition is formulated into a preparation is less than 10 mg, the plasma concentration of the active ingredient when the preparation is applied to humans is insufficient to exhibit an analgesic action, and if it exceeds 400 mg, most of the patients will be overdosed although the amount of morphine necessary for pain therapy varies among individuals. Therefore, such amount is not preferred.

Incidentally, in the test using the above-mentioned white rabbit, if hair removal is performed using a hair removal cream or the like after the shaving treatment, the skin is damaged and the transdermal absorption rate of the active ingredient is accelerated, which has a great influence on the available amount and plasma concentration of the active ingredient, and therefore, caution is necessary.

Further, the above-mentioned "single dose of the preparation" means the total dose per single administration when the preparation is applied. If plural preparations are applied to two or more sites in a single administration, the total application amount should be the single dose of the preparation.

Further, the medicinal composition of the invention should meet the requirement that the plasma concentrations of the active ingredient 24 hours and 48 hours after the application of the preparation under the above-mentioned conditions are each at least 40 ng/mL in terms of morphine base.

The plasma concentrations of the active ingredient 24 hours and 48 hours after the application of the preparation are each generally 50 ng/mL or more, preferably 70 ng/mL or more, more preferably 90 ng/mL or more in terms of morphine base although they vary depending on the dose of the preparation. If either of the plasma concentrations of the active ingredient 24 hours and 48 hours after the application of the preparation is less than 40 ng/mL, the plasma concentrations of the active ingredient 24 hours and 48 hours after the application of the preparation when the preparation is applied to humans are insufficient to exhibit an analgesic action, which is not preferred.

Further, the medicinal composition of the invention has at least a portion of the active ingredient in a crystalline form. The ratio of the active ingredient in a crystalline form to be held in the above-mentioned active ingredient-holding vehicle to the total amount of the active ingredient is not particularly limited as long as an appropriate transdermal absorption rate can be obtained when the preparation is applied. The content amount of the active ingredient in a crystalline form is generally 30% by mass or more, preferably 40% by mass or more, more preferably 50% by mass or more, and particularly preferably 60% by mass or more.

If the ratio of the active ingredient in a crystalline form to be held is less than 30% by mass, the availability of the active ingredient in the medicinal composition is decreased as described below and moreover, transdermal absorption is also deteriorated, which is not preferred.

The medicinal composition of the invention is produced by blending morphine or a salt thereof serving as the active ingredient in the active ingredient-holding vehicle according to a common procedure as described above. It is preferred to further include therein a transdermal absorption accelerator.

The transdermal absorption accelerator is a component having an effect of accelerating the transdermal absorption of the active ingredient; in other words, if a certain component is contained in the medicinal composition and the transdermal absorption of the active ingredient is accelerated due to the presence of the component, it can be said that such component is the transdermal absorption accelerator for the active ingredient.

The transdermal absorption accelerator is preferably uniformly mixed in the active ingredient-holding vehicle. However, even if the combination is such that the transdermal absorption accelerator undergoes separation over time, such transdermal absorption accelerator can still be used as long as the degree of the undergoes separation is not practically problematic when the transdermal absorption accelerator is carried, for example, on the below-mentioned medicinal composition storing unit.

The type of the transdermal absorption accelerator is not particularly limited as long as it has an effect of accelerating the transdermal absorption of the active ingredient; however, for example, one or more compounds selected from a saturated higher fatty acid, an unsaturated higher fatty acid, a higher alcohol, an alkylene oxide adduct of a higher alcohol, a crotonotoluidine derivative and hydroxy acid can be given. More specifically, one or more compounds selected from lauric acid, palmitic acid, oleic acid, oleyl alcohol, polyoxyethylene lauryl ether, crotamiton and lactic acid can be given as examples. Among them, lauric acid, oleic acid, oleyl alcohol and polyoxyethylene lauryl ether can be advantageously used.

Further, in the active ingredient-holding vehicle, water may be included to such an extent that the transdermal absorption and availability of the active ingredient are not significantly decreased. However, as described below, when the water content in the active ingredient-holding vehicle is increased, the availability of the active ingredient is decreased and moreover, the transdermal absorption is also deteriorated, and thus, it is preferred that water is not at all blended or the blending ratio thereof is kept low. However, since water functions to reduce skin irritation, it may be added in an appropriate amount by considering the balance between the skin irritation and the transdermal absorption of the active ingredient.

In particular, if the water content in the total medicinal composition is 50% by mass or more, the practicability is decreased due to the above-mentioned reason, and therefore, the water content in the medicinal composition is preferably less than 50% by mass. The water content in the medicinal composition is generally less than 30% by mass, preferably less than 20% by mass, more preferably less than 15% by mass, particularly preferably less than 10% by mass.

To the medicinal composition of the invention, another active ingredient or any of a variety of arbitrary components acceptable as additives for medicinal products can be appropriately added in a necessary amount as needed as long as it does not hinder the effect of the invention.

Examples of the arbitrary components which can be blended include other medicinal active ingredients, a skin irritation reducing agent, a stabilizing agent, a pH adjusting agent, a viscosity controlling agent, a crosslinking agent, an antioxidant, a preservative, an emulsifying agent, an antiseptic and a solubilizing agent.

Examples of the other medicinal active ingredients which can be added include a nonopioid analgesic selected from aspirin, naproxen, acetaminophen, loxoprofen, ibuprofen, diclofenac, indomethacin or salts thereof; an opioid analgesic selected from opium, opiate alkaloid, scopolamine, ethylmorphine, oxycodone, pethidine, codeine, dihydrocodeine, fentanyl, droperidol, oxymetebanol, levorphanol, propoxyphene, methadone, hydromorphone, meperidine, buprenorphine, butorphanol, pentazocine, dezocine, tramadol, eptazocine or salts thereof; and an analgesic adjuvant belonging to a category of antiepileptic, antidepressant, antiarrhythmic or corticosteroid selected from carbamazepine, valproic acid, clonazepam, amitriptyline, imipramine, amoxapine, mexiletine, prednisolone, dexamethasone or salts thereof.

Further, examples of the skin irritation reducing agent which can be blended include a polyhydric alcohol such as glycerin, and examples of the antioxidant which can be blended include sodium thiosulfate and butylated hydroxytoluene. Among these, particularly glycerin has a strong skin irritation reducing effect and can be advantageously used. The blending amount of glycerin is preferably from 5 to 70% by mass, more preferably from 10 to 60% by mass, particularly preferably from 20 to 50% by mass.

The medicinal composition obtained as described above can be used, as in a simple way, by putting an appropriate amount thereof in, for example, a plastic container and fixing the container to the skin of a patient to be treated with a tape or the like. By further improving the dosage form, a higher effect can be expected.

As one example of the above-mentioned dosage form, a medicinal composition storing unit having a structure in which the medicinal composition is carried on a support having voids such that the active ingredient-holding vehicle can move in the support can be given. By doing this, the medicinal composition of the invention can be more advantageously used.

As the support having voids, one member or a mixture or a complex of two or more members selected from a compressed body of a fibrous substance, a compressed body of a powdery substance and a sponge foam can be given.

Here, the compressed body of a fibrous substance is preferably a flat plate formed of a cellulose fiber typified by a filter paper or the like from the economical viewpoint.

Further, when a sponge foam is used as the support, the sponge foam preferably has an open-cell structure from the viewpoint of ability to hold the medicinal composition and sustained releasability. The sponge foam is preferably formed of one or more materials selected from a plastic and a rubber. In particular, the plastic is preferably one or more compounds selected from polyethylene, polypropylene, polyurethane, polyethylene terephthalate and polyvinyl acetate.

In addition, according to a technique disclosed in WO 99/14283, WO 00/06659 or the like other than the above-mentioned method, any of various types of gel is used as the support having voids and the medicinal composition of the invention may be held in the meshwork thereof.

The holding amount of the medicinal composition per single dose of the medicinal composition storing unit obtained as described above can be freely adjusted as long as it falls within a range capable of providing appropriate transdermal absorption rate and transdermal absorption duration. However, particularly, it is preferably adjusted to a range of from 0.1 g to 10 g. The medicinal composition per single dose of the medicinal composition storing unit is generally preferably from 0.5 g to 6 g, more preferably from 1 g to 4 g, particularly preferably from 1.5 g to 3 g. If the medicinal composition for transdermal absorption per single dose of the medicinal composition storing unit is less than 0.1 g, the amount is not sufficient for allowing the active ingredient to be sufficiently absorbed, and therefore, it is not preferred. Meanwhile, if it exceeds 10 g, the medicinal composition storing unit is expanded in size to deteriorate the patients' QOL when the transdermal absorption preparation is applied, which is not preferred.

Further, the effective transdermal absorption area per single dose of the medicinal composition storing unit is from 3 $cm^2$ to 100 $cm^2$, generally preferably from 4 $cm^2$ to 80 $cm^2$, more preferably from 5 $cm^2$ to 60 $cm^2$, further more preferably from 6 $cm^2$ to 50 $cm^2$, particularly preferably from 7 $cm^2$ to 40 $cm^2$. If the effective transdermal absorption area per single dose of the medicinal composition storing unit is less than 3 $cm^2$, when the active ingredient is administered at a high dose, it is necessary to set the drug absorption amount per unit area significantly high which results in imposing too much burden on the skin, which is not preferred. Meanwhile, if it exceeds 100 $cm^2$, due to the size, the patients' QOL is deteriorated when the transdermal absorption preparation is applied, which is not preferred.

Further, the void ratio of the support to be used in the medicinal composition storing unit is not particularly limited as long as a good balance of shape retainability, flexibility, ability to hold the active ingredient-holding vehicle per unit area of the support and amount of the medicinal composition remaining on the skin at the time of completion of application can be maintained. In general, it is from 50% to 95%, preferably from 60% to 90%, more preferably from 70% to 85%. If the void ratio is less than 50%, the support is poor in flexibility and ability to hold the active ingredient-holding vehicle per unit area of the support, which is not preferred. Meanwhile, if it exceeds 95%, the shape retainability is low, and also the amount of the medicinal composition remaining on the skin at the time of completion of application is increased, which is not preferred.

In the above-mentioned medicinal composition storing unit, the active ingredient in a crystalline form may be carried uniformly or locally, or localized and carried, the latter being particularly preferable. It is presumed that when the active ingredient is localized and carried, a contact ratio of the active ingredient and the active ingredient-holding vehicle is decreased thereby improving the sustained releasability of the active ingredient. The medicinal composition storing unit can be used without any problems whether the site where the active ingredient is localized is in the interior of the support constituting the medicinal composition storing unit or on the surface thereof. However, the site is particularly preferably on the surface of the support from the viewpoint of production cost and sustained releasability.

The medicinal composition storing unit of the invention described above can be produced by any of various known methods. As a specific method, a method in which a given amount of the previously prepared medicinal composition is dropped on or injected into the support having voids to produce the unit can be given as an example. More specifically, for example, in the case where the support is a flat plate formed of a cellulose fiber typified by a filter paper, the unit can be produced by dropping a given amount of the previously prepared medicinal composition for transdermal absorption on this cellulose disk. Further, as described above, it can also be produced by a technique disclosed in WO 99/14283, WO 00/06659 or the like.

If the above-mentioned medicinal composition storing unit has sufficient adhesiveness, it may be applied to the skin as such, and if it has low adhesiveness or does not have adhesiveness, it can be used by fixing it on the skin of a patient to be treated with a tape or the like. Further, in order to facilitate the use thereof, it is preferred that by using this medicinal composition storing unit, a transdermal absorption preparation as schematically shown in FIG. 1 is prepared.

As shown in FIG. 1, it is more preferred to prepare a transdermal absorption preparation 1 by sequentially laminating an impermeable layer 3 which practically does not allow the active ingredient and the active ingredient-holding vehicle to permeate therethrough, an adhesive layer 5 and an adhesive holding layer 6 on the surface opposite to the surface to be applied to the skin of a medicinal composition storing unit 2, and laminating a drug protecting layer 4 and a release film 7 on the surface to be applied to the skin of the medicinal composition storing unit 2.

The material of the impermeable layer 3 to be used in the transdermal absorption preparation 1 can be any material as long as it practically does not allow the active ingredient and the active ingredient-holding vehicle to permeate therethrough. Specifically, a plastic such as vinyl chloride, polyethylene, polypropylene or polyethylene terephthalate, a metal such as stainless steel or aluminum, cellophane and a silicone resin can be given as examples. Among these, particularly vinyl chloride, polyethylene, polypropylene, polyethylene terephthalate or aluminum is preferred.

As described above, the medicinal composition storing unit can be used without any problems whether the place where the active ingredient is localized is in the interior of the support constituting the medicinal composition storing unit or on the surface thereof. However, in the case where the medicinal composition storing unit is produced by dropping the composition for transdermal absorption on the support, unless the void size of the support is sufficiently larger than the particle size of the active ingredient, the crystals of the active ingredient are captured in the vicinity of the surface of the support. As a result, the active ingredient is localized in the vicinity of the surface of the support. Accordingly, in such a case, it is preferred that the active ingredient is localized on the surface of the medicinal composition storing unit.

Further, in the case where the active ingredient is localized on the surface as described above, when the preparation is applied as it is with the surface carrying the active ingredient facing the skin, the powder of the active ingredient may remain on the skin at the time of completion of application of the preparation depending on the availability of the active ingredient, which is not preferred. Accordingly, it is preferred to place the powder of the active ingredient on the surface opposite to the surface to be applied to the skin or to provide the drug protecting layer 4 having liquid permeability for retaining the powder of the active ingredient to cover the powder of the active ingredient.

As a specific example of the drug protecting layer 4 having liquid permeability, a film made of cellulose, cellulose acetate, nitrocellulose or a porous plastic film can be given. Among these, a flat plate formed of a cellulose fiber, a membrane filter formed of a cellulose mixed ester (cellulose acetate and nitrocellulose) or a microporous plastic film is preferred, and particularly preferred is a microporous plastic film.

Further, the transdermal absorption preparation of the invention preferably has a release film 7 to be released at the time of use on the surface to be applied to the skin of the medicinal composition storing unit 2.

The transdermal absorption preparation described above can be produced by any of various known methods, and as the adhesive layer 5, the adhesive holding layer 6 and the release film 7 to be used for the preparation, known materials can be used. As one example of the specific production methods, a method in which the drug protecting layer 4 is provided as needed on the previously produced medicinal composition storing unit 2, and further, any type of drug impermeable layer 3, adhesive layer 5 and adhesive holding layer 6 are laminated on the surface opposite to the surface to be applied to the skin can be given. In particular, when a member in which the adhesive layer 5 and the adhesive holding layer 6 have previously been integrated is used, the preparation can be more efficiently produced.

According to the invention, it has become possible to provide a sustained release transdermal absorption preparation of morphine or a salt thereof which had not been achieved by anyone although several attempts were made worldwide in the past. This is an innovative preparation which significantly improves patients' QOL in the world who suffer from pain, particularly cancer pain.

It is not necessarily clear at present by what mechanism morphine or a salt thereof is transdermally absorbed or the release thereof is sustained when the medicinal composition, medicinal composition unit or transdermal absorption preparation of the invention is applied. Although the following description is a mere conjecture by the inventors of the present application because of this reason, basically, the mechanism is roughly considered to be as follows.

(1) As compared with common transdermal absorption preparations, due to the excessive presence of the active ingredient-holding vehicle (usually liquid or semi-solid) having fluidity, the skin is put in a highly humid state, and therefore, the barrier function of the skin is reduced.

(2) The active ingredient in a dissolved form penetrates into the blood vessel under the skin along with the transdermal absorption accelerator and is absorbed.

(3) When the active ingredient in a dissolved form is decreased, the active ingredient in a crystalline form is dissolved in the active ingredient-holding vehicle to compensate the decrease. In this manner, sustained release is achieved.

(4) Further, by carrying the medicinal composition on the support having voids to form the medicinal composition storing unit, the flow of the active ingredient-holding vehicle is moderately inhibited and higher sustained releasability is realized.

(5) In addition, by placing the drug-impermeable layer on the back surface of the medicinal composition storing unit, an occlusive dressing technique (ODT) is accomplished, and transdermal absorption is further improved.

EXAMPLES

Hereinafter the present invention will be described in detail by showing Examples, though the invention is by no means limited to these Examples.

Example 1

10.0 parts by mass of morphine hydrochloride (manufactured by Sankyo Company, Limited, Japanese Pharmacopoeia, morphine hydrochloride, water content: 14.4%), 6.3 parts by mass of liquid paraffin, 40.7 parts by mass of propylene glycol, 20.3 parts by mass of polyethylene glycol 400, 2.7 parts by mass of crotamiton, 5.6 parts by mass of oleyl alcohol, 13.7 parts by mass of polyoxyethylene (9) lauryl ether and 0.7 parts by mass of lactic acid were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, about 1.4 g of thus obtained medicinal composition for transdermal absorption was taken with a Pasteur pipette and dropped uniformly on the whole area of a cellulose disk (manufactured by Advantec Toyo Kaisha, Ltd. absorbent pad for liquid medium, Model No: M-085, diameter: about 47 mm, thickness: about 1 mm), whereby a medicinal composition storing unit was produced.

Further, on the surface of the medicinal composition storing unit on which the medicinal composition for transdermal absorption was dropped, a membrane filter (manufactured by Millipore Corporation, Model No: HAWP-04700, pore size: 0.45 µm, diameter: 47 mm, formed of a cellulose mixed ester (cellulose acetate+nitrocellulose)) was placed as a drug protecting layer. Further, on the surface opposite to the surface on which the medicinal composition for transdermal absorption was dropped, an adhesive tape in which an acrylic adhesive was laminated on a vinyl chloride film (manufactured by Kyowa Limited, Model No: AKH-HZL 60µ, film thickness: 60 µm, total thickness: about 100 µm) and which was cut into a circle with a diameter of about 70 mm was placed as an impermeable layer, and on the back surface thereof, further a polyurethane film (manufactured by Kyowa Limited, Million Aid Dressing Tape, Model No: MA-E150-A, thickness: 30

μm) which was cut into about 15 cm×15 cm was placed as an adhesive layer and an adhesive holding layer, whereby a transdermal absorption preparation was obtained.

Thus obtained preparation was used such that one set including two sheets thereof was given as a single dose at the time of application, and the blending amount of the active ingredient per single dose in terms of base was 213 mg.

Example 2

10.0 parts by mass of morphine hydrochloride, 6.3 parts by mass of liquid paraffin, 40.7 parts by mass of propylene glycol, 20.3 parts by mass of polyethylene glycol 400, 2.7 parts by mass of crotamiton, 5.6 parts by mass of oleyl alcohol, 13.7 parts by mass of polyoxyethylene (9) lauryl ether and 0.7 parts by mass of lactic acid were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, about 1.4 g of thus obtained medicinal composition for transdermal absorption was taken with a Pasteur pipette and dropped uniformly on the whole area of a cellulose disk (manufactured by Advantec Toyo Kaisha, Ltd. absorbent pad for liquid medium, Model No: M-085, diameter: about 47 mm, thickness: about 1 mm), whereby a medicinal composition storing unit A was produced. Further, by the same procedure, about 1.3 g of the medicinal composition for transdermal absorption was dropped on another absorbent pad for liquid medium of the same type, whereby a medicinal composition storing unit B was produced. Thereafter, the unit B was laminated on the unit A such that the surface of the unit B on which the composition was dropped faced the surface of the unit A on which the composition was not dropped, whereby a medicinal composition storing unit was obtained.

Further, on the medicinal composition storing unit comprising the unit A and the unit B, on the surface thereof on which the medicinal composition for transdermal absorption was dropped, a membrane filter (manufactured by Millipore Corporation, Model No: HAWP-04700, pore size: 0.45 μm, diameter: 47 mm, formed of a cellulose mixed ester (cellulose acetate+nitrocellulose)) was placed as a drug protecting layer. Further, on the surface opposite to the surface on which the medicinal composition for transdermal absorption was dropped, an adhesive tape in which an acrylic adhesive was laminated on a vinyl chloride film (manufactured by Kyowa Limited, Model No: AKH-HZL 60μ, film thickness: 60 μm, total thickness: about 100 μm) and which was cut into a circle with a diameter of about 70 mm was placed as an impermeable layer, and on the back surface thereof, further a polyurethane film (manufactured by Kyowa Limited, Million Aid Dressing Tape, Model No: MA-E150-A, thickness: 30 μm) which was cut into about 15 cm×15 cm was placed as an adhesive layer and an adhesive holding layer, whereby a transdermal absorption preparation was obtained.

Thus obtained preparation was used such that one set including two sheets thereof was given as a single dose at the time of application, and the blending amount of the active ingredient per single dose in terms of base was 410 mg.

Example 3

20.0 parts by mass of morphine hydrochloride, 23.4 parts by mass of propylene glycol, 13.3 parts by mass of polyethylene glycol 400, 23.3 parts by mass of oleyl alcohol and 20.0 parts by mass of polyoxyethylene (9) lauryl ether were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, about 1.4 g of thus obtained medicinal composition for transdermal absorption was taken with a Pasteur pipette and dropped uniformly on the whole area of an open-cell polyethylene sponge foam (manufactured by Inoac Corporation, trade name: MAPS, Model No: ST-15, cell size: about 55 μm, void ratio: about 85%, thickness: about 1 mm) which was punched out into a circle with a diameter of about 47 mm, whereby a medicinal composition storing unit was produced.

Further, on the surface of the medicinal composition storing unit on which the medicinal composition for transdermal absorption was dropped, an adhesive tape in which an acrylic adhesive was laminated on a vinyl chloride film (manufactured by Kyowa Limited, Model No: AKH-HZL 60μ, film thickness: 60 μm, total thickness: about 100 μm) and which was cut into a circle with a diameter of about 70 mm was placed as an impermeable layer, and on the back surface thereof, further a polyurethane film (manufactured by Kyowa Limited, Million Aid Dressing Tape, Model No: MA-E150-A, thickness: 30 μm) which was cut into about 15 cm×15 cm was placed as an adhesive layer and an adhesive holding layer, whereby a transdermal absorption preparation was obtained.

Thus obtained preparation was used such that one sheet thereof was given as a single dose at the time of application, and the blending amount of the active ingredient per single dose in terms of base was 213 mg.

Example 4

20.0 parts by mass of morphine hydrochloride, 23.4 parts by mass of propylene glycol, 13.3 parts by mass of polyethylene glycol 400, 23.3 parts by mass of oleyl alcohol and 20.0 parts by mass of polyoxyethylene (9) lauryl ether were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, about 1.4 g of thus obtained medicinal composition for transdermal absorption was taken with a Pasteur pipette and dropped uniformly on the whole area of an open-cell polyethylene sponge foam (manufactured by Inoac Corporation, trade name: MAPS, Model No: ST-15, cell size: about 55 μm, void ratio: about 85%, thickness: about 1 mm) which was punched out into a circle with a diameter of about 47 mm, whereby a medicinal composition storing unit was produced.

Further, on the surface of the medicinal composition storing unit on which the medicinal composition for transdermal absorption was dropped, an adhesive tape in which an acrylic adhesive was laminated on a vinyl chloride film (manufactured by Kyowa Limited, Model No: AKH-HZL 60μ, film thickness: 60 μm, total thickness: about 100 μm) and which was cut into a circle with a diameter of about 70 mm was placed as an impermeable layer, and on the back surface thereof, further a polyurethane film (manufactured by Kyowa Limited, Million Aid Dressing Tape, Model No: MA-E150-A, thickness: 30 μm) which was cut into about 15 cm×15 cm was placed as an adhesive layer and an adhesive holding layer.

Further, on the surface opposite to the surface on which the medicinal composition for transdermal absorption was dropped, a porous polypropylene film (diameter: about 70 mm, thickness: about 60 μm, pore size: about 500 μm, aperture ratio: about 9%) was placed, whereby a transdermal absorption preparation was obtained.

Thus obtained preparation was used such that one sheet thereof was given as a single dose at the time of application, and the blending amount of morphine per single dose in terms of base was 213 mg.

Example 5

10.0 parts by mass of morphine hydrochloride, 40.0 parts by mass of 1,3-butylene glycol, 25.0 parts by mass of polyethylene glycol 400, 10.0 parts by mass of oleyl alcohol and 15.0 parts by mass of polyoxyethylene (9) lauryl ether were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, thus obtained medicinal composition for transdermal absorption was treated in the same manner as in Example 1, whereby a medicinal composition storing unit was produced.

Further, on the surface of the medicinal composition storing unit on which the medicinal composition for transdermal absorption was dropped, a membrane filter (manufactured by Millipore Corporation, Model No: HAWP-04700, pore size: 0.45 µm, diameter: 47 mm, formed of a cellulose mixed ester (cellulose acetate+nitrocellulose)) was placed as a drug protecting layer. Further, on the surface opposite to the surface on which the medicinal composition for transdermal absorption was dropped, a polyurethane film (manufactured by Kyowa Limited, Million Aid Dressing Tape, Model No: MA-E150-A, thickness: 30 µm) which was cut into about 15 cm×15 cm was placed as an adhesive layer and an adhesive holding layer, whereby a transdermal absorption preparation was obtained.

Thus obtained preparation was used such that one set including two sheets thereof was given as a single dose at the time of application, and the blending amount of morphine per single dose in terms of base was 213 mg.

Example 6

10.0 parts by mass of morphine hydrochloride, 66.8 parts by mass of a silicone oil (1000 cSt), 2.5 parts by mass of crotamiton, 6.0 parts by mass of oleyl alcohol, 14.0 parts by mass of polyoxyethylene (9) lauryl ether and 0.7 parts by mass of lactic acid were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, thus obtained medicinal composition for transdermal absorption was treated in the same manner as in Example 1, whereby a medicinal composition storing unit was produced.

Further, thus obtained medicinal composition storing unit was processed in the same manner as in Example 1, whereby a transdermal absorption preparation was obtained.

Thus obtained preparation was used such that one set including two sheets thereof was given as a single dose at the time of application, and the blending amount of morphine per single dose in terms of base was 213 mg.

Example 7

10.0 parts by mass of morphine hydrochloride, 5.0 parts by mass of liquid paraffin, 40.0 parts by mass of propylene glycol, 20.0 parts by mass of polyethylene glycol 400 and 25.0 parts by mass of oleyl alcohol were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, thus obtained medicinal composition for transdermal absorption was treated in the same manner as in Example 1, whereby a medicinal composition storing unit was produced.

Further, thus obtained medicinal composition storing unit was treated in the same manner as in Example 1, whereby a transdermal absorption preparation was obtained.

Thus obtained preparation was used such that one set including two sheets thereof was given as a single dose at the time of application, and the blending amount of morphine per single dose in terms of base was 213 mg.

Example 8

10.0 parts by mass of morphine hydrochloride, 5.0 parts by mass of liquid paraffin, 40.0 parts by mass of propylene glycol, 20.0 parts by mass of polyethylene glycol 400 and 25.0 parts by mass of polyoxyethylene (9) lauryl ether were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, thus obtained medicinal composition for transdermal absorption was treated in the same manner as in Example 1, whereby a medicinal composition storing unit was produced.

Further, thus obtained medicinal composition storing unit was treated in the same manner as in Example 1, whereby a transdermal absorption preparation was obtained.

Thus obtained preparation was used such that one set including two sheets thereof was given as a single dose at the time of application, and the blending amount of morphine per single dose in terms of base was 213 mg.

Example 9

10.0 parts by mass of morphine hydrochloride, 5.0 parts by mass of liquid paraffin, 40.0 parts by mass of propylene glycol, 20.0 parts by mass of polyethylene glycol 400 and 25.0 parts by mass of lauric acid were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, thus obtained medicinal composition for transdermal absorption was treated in the same manner as in Example 1, whereby a medicinal composition storing unit was produced.

Further, thus obtained medicinal composition storing unit was treated in the same manner as in Example 1, whereby a transdermal absorption preparation was obtained.

Thus obtained preparation was used such that one set including two sheets thereof was given as a single dose at the time of application, and the blending amount of morphine per single dose in terms of base was 213 mg.

Example 10

10.0 parts by mass of morphine hydrochloride, 5.0 parts by mass of liquid paraffin, 40.0 parts by mass of propylene glycol, 20.0 parts by mass of polyethylene glycol 400 and 25.0 parts by mass of oleic acid were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, thus obtained medicinal composition for transdermal absorption was treated in the same manner as in Example 1, whereby a medicinal composition storing unit was produced.

Further, thus obtained medicinal composition storing unit was treated in the same manner as in Example 1, whereby a transdermal absorption preparation was obtained.

Thus obtained preparation was used such that one set including two sheets thereof was given as a single dose at the time of application, and the blending amount of morphine per single dose in terms of base was 213 mg.

Example 11

10.0 parts by mass of morphine hydrochloride, 10.0 parts by mass of oleyl alcohol, 15.0 parts by mass of polyoxyethylene (9) lauryl ether, 11.0 parts by mass of ceramide, 11.0 parts by mass of cholesterol and 43.0 parts by mass of isopropyl palmitate were mixed by heating to about 50° C., and the resulting mixture was stirred for about 1 minute in an ultrasonic bath to uniformly disperse morphine hydrochloride, whereby a medicinal composition for transdermal absorption as a pale yellow-white suspension liquid was obtained.

Subsequently, thus obtained medicinal composition for transdermal absorption was treated in the same manner as in Example 1, whereby a medicinal composition storing unit was produced.

Further, thus obtained medicinal composition storing unit was treated in the same manner as in Example 1, whereby a transdermal absorption preparation was obtained.

Thus obtained preparation was used such that one set including two sheets thereof was given as a single dose at the time of application, and the blending amount of morphine per single dose in terms of base was 213 mg.

Example 12

10.0 parts by mass of morphine hydrochloride, 41.5 parts by mass of polyethylene glycol 400, 10.0 parts by mass of oleyl alcohol, 15.0 parts by mass of polyoxyethylene (9) lauryl ether, 5.0 parts by mass of ceramide, 5.0 parts by mass of cholesterol, 10.2 parts by mass of isopropyl palmitate and 3.3 parts by mass of palmitic acid were mixed by heating to about 50° C., and the resulting mixture was stirred for about 1 minute in an ultrasonic bath to uniformly disperse morphine hydrochloride, whereby a medicinal composition for transdermal absorption as a pale yellow-white suspension liquid was obtained.

Subsequently, thus obtained medicinal composition for transdermal absorption was treated in the same manner as in Example 1, whereby a medicinal composition storing unit was produced.

Further, thus obtained medicinal composition storing unit was treated in the same manner as in Example 1, whereby a transdermal absorption preparation was obtained.

Thus obtained preparation was used such that one set including two sheets thereof was given as a single dose at the time of application, and the blending amount of morphine per single dose in terms of base was 213 mg.

Example 13

9.7 parts by mass of morphine hydrochloride, 40.2 parts by mass of polyethylene glycol 400, 3.2 parts by mass of polyvinylpyrrolidone, 9.7 parts by mass of oleyl alcohol, 14.5 parts by mass of polyoxyethylene (9) lauryl ether, 4.8 parts by mass of ceramide, 4.8 parts by mass of cholesterol, 9.9 parts by mass of isopropyl palmitate and 3.2 parts by mass of palmitic acid were mixed by heating to about 50° C., and the resulting mixture was stirred for about 1 minute in an ultrasonic bath to uniformly disperse morphine hydrochloride, whereby a medicinal composition for transdermal absorption as a pale yellow-white suspension liquid was obtained.

Subsequently, thus obtained medicinal composition for transdermal absorption was treated in the same manner as in Example 1, whereby a medicinal composition storing unit was produced.

Further, thus obtained medicinal composition storing unit was treated in the same manner as in Example 1, whereby a transdermal absorption preparation was obtained.

Thus obtained preparation was used such that one set including two sheets thereof was given as a single dose at the time of application, and the blending amount of morphine per single dose in terms of base was 207 mg.

Comparative Example 1

10.0 parts by mass of morphine hydrochloride, 26.5 parts by mass of an ester gum, 17.5 parts by mass of polyvinyl acetate, 2.0 parts by mass of liquid paraffin, 20.0 parts by mass of propylene glycol, 10.0 parts by mass of polyethylene glycol 400, 2.0 parts by mass of crotamiton, 5.0 parts by mass of polyoxyethylene (9) lauryl ether, 2.0 parts by mass of sorbitan monoleate and 5.0 parts by mass of kaolin were mixed by heating to about 50° C., whereby a muddy medicinal composition for transdermal absorption was obtained.

Thus obtained composition was applied to a film in which a polyethylene terephthalate film was laminated on a non-woven cloth, and further, a silicone-coated paper release film was placed on the surface to which the composition was applied. Then, the resulting article was punched out into a square with a side length of 5.5 cm, whereby a transdermal absorption preparation was obtained.

Thus obtained preparation was used such that two sheets thereof were given as a single dose at the time of application. The blending amount of morphine per single dose in terms of base was 155 mg.

Comparative Example 2

10.0 parts by mass of morphine hydrochloride, 24.0 parts by mass of an ester gum, 15.0 parts by mass of polyvinyl acetate, 2.0 parts by mass of liquid paraffin, 20.0 parts by mass of propylene glycol, 10.0 parts by mass of polyethylene glycol 400, 2.0 parts by mass of crotamiton, 5.0 parts by mass of polyoxyethylene (9) lauryl ether, 2.0 parts by mass of sorbitan monoleate and 10.0 parts by mass of magnesium stearate were mixed by heating to about 50° C., whereby a muddy medicinal composition for transdermal absorption was obtained.

Thus obtained composition was applied to a film in which a polyethylene terephthalate film was laminated on a non-woven cloth, and further, a silicone-coated paper release film was placed on the surface to which the composition was applied. Then, the resulting article was punched out into a square with a side length of 5.5 cm, whereby a transdermal absorption preparation was obtained.

Thus obtained preparation was used such that two sheets thereof were given as a single dose at the time of application. The blending amount of morphine per single dose in terms of base was 74 mg.

Comparative Example 3

19.8 parts by mass of morphine hydrochloride, 49.4 parts by mass of a styrene-isoprene-styrene block copolymer, 24.8 parts by mass of an ester gum, 5.0 parts by mass of polyoxyethylene (9) lauryl ether and 1.0 parts by mass of lactic acid were mixed by heating to about 160° C., whereby a semi-solid medicinal composition for transdermal absorption was obtained.

Thus obtained composition was applied to a polyethylene terephthalate film, and further a silicone-coated polyethylene terephthalate release film was placed on the surface to which the composition was applied. Then, the resulting article was punched out into a square with a side length of 2.8 cm, whereby a transdermal absorption preparation was obtained.

Thus obtained preparation was used such that ten sheets thereof were given as a single dose at the time of application. The blending amount of morphine per single dose in terms of base was 289 mg.

Comparative Example 4

10.0 parts by mass of morphine hydrochloride, 25.7 parts by mass of an ester gum, 31.2 parts by mass of polyvinyl acetate, 2.3 parts by mass of liquid paraffin, 15.0 parts by mass of propylene glycol, 7.5 parts by mass of polyethylene glycol 400, 1.0 parts by mass of crotamiton, 2.0 parts by mass of oleyl alcohol, 5.0 parts by mass of polyoxyethylene (9) lauryl ether and 0.3 parts by mass of lactic acid were mixed by heating to about 50° C., whereby a muddy medicinal composition for transdermal absorption was obtained.

Thus obtained composition was applied to a polyethylene terephthalate film, and further a silicone-coated polyethylene terephthalate release film was placed on the surface to which the composition was applied. Then, the resulting article was punched out into a square with a side length of 5.5 cm, whereby a transdermal absorption preparation was obtained.

Thus obtained preparation was used such that two sheets thereof were given as a single dose at the time of application. The blending amount of morphine per single dose in terms of base was 166 mg.

Comparative Example 5

10.0 parts by mass of morphine hydrochloride, 25.7 parts by mass of an ester gum, 31.2 parts by mass of polyvinyl acetate, 2.3 parts by mass of liquid paraffin, 15.0 parts by mass of propylene glycol, 7.5 parts by mass of polyethylene glycol 400, 1.0 parts by mass of crotamiton, 2.0 parts by mass of oleyl alcohol, 5.0 parts by mass of polyoxyethylene (9) lauryl ether and 0.3 parts by mass of lactic acid were mixed by heating to about 50° C., whereby a muddy medicinal composition for transdermal absorption was obtained.

Thus obtained composition was applied to a film in which a polyethylene terephthalate film was laminated on a nonwoven cloth, and further, a silicone-coated paper release film was placed on the surface to which the composition was applied. Then, the resulting article was punched out into a square with a side length of 5.5 cm, whereby a transdermal absorption preparation was obtained.

Thus obtained preparation was used such that two sheets thereof were given as a single dose at the time of application. The blending amount of morphine per single dose in terms of base was 126 mg.

Comparative Example 6

10.0 parts by mass of morphine hydrochloride, 8.4 parts by mass of liquid paraffin, 54.4 parts by mass of propylene glycol and 27.2 parts by mass of polyethylene glycol 400 were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, thus obtained medicinal composition for transdermal absorption was treated in the same manner as in Example 1, whereby a medicinal composition storing unit was produced.

Further, thus obtained medicinal composition storing unit was treated in the same manner as in Example 1, whereby a transdermal absorption preparation was obtained.

Thus obtained preparation was used such that one set including two sheets thereof was given as a single dose at the time of application. The blending amount of morphine per single dose in terms of base was 213 mg.

Comparative Example 7

10.0 parts by mass of morphine hydrochloride, 66.8 parts by mass of glycerin, 2.5 parts by mass of crotamiton, 6.0 parts by mass of oleyl alcohol, 14.0 parts by mass of polyoxyethylene (9) lauryl ether and 0.7 parts by mass of lactic acid were mixed, whereby a clear and colorless medicinal composition for transdermal absorption was obtained.

Subsequently, thus obtained medicinal composition for transdermal absorption was treated in the same manner as in Example 1, whereby a medicinal composition storing unit was produced.

Further, thus obtained medicinal composition storing unit was treated in the same manner as in Example 1, whereby a transdermal absorption preparation was obtained.

Thus obtained preparation was used such that one set including two sheets thereof was given as a single dose at the time of application. The blending amount of morphine per single dose in terms of base was 213 mg.

Comparative Example 8

10.0 parts by mass of morphine hydrochloride, 2.8 parts by mass of liquid paraffin, 18.0 parts by mass of propylene glycol, 9.0 parts by mass of polyethylene glycol 400, 1.3 parts by mass of crotamiton, 2.5 parts by mass of oleyl alcohol, 6.1 parts by mass of polyoxyethylene (9) lauryl ether, 0.3 parts by mass of lactic acid and 50.0 parts by mass of water were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, thus obtained medicinal composition for transdermal absorption was treated in the same manner as in Example 1, whereby a medicinal composition storing unit was produced.

Further, thus obtained medicinal composition storing unit was treated in the same manner as in Example 1, whereby a transdermal absorption preparation was obtained.

Thus obtained preparation was used such that one set including two sheets thereof was given as a single dose at the time of application. The blending amount of morphine per single dose in terms of base was 213 mg.

Comparative Example 9

20.0 parts by mass of morphine hydrochloride, 5.6 parts by mass of liquid paraffin, 36.2 parts by mass of propylene glycol, 18.0 parts by mass of polyethylene glycol 400, 2.5 parts by mass of crotamiton, 5.0 parts by mass of oleyl alcohol, 12.1 parts by mass of polyoxyethylene (9) lauryl ether and 0.6 parts by mass of lactic acid were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, 2.8 g of thus obtained medicinal composition for transdermal absorption was taken with a Pasteur pipette and put in a 6 cm×6 cm square bag formed of an ethylene vinyl acetate copolymer film (thickness: 40 μm, content of vinyl acetate: about 10%). The bag was heat-sealed such that a very small amount of air was left therein, whereby a reservoir preparation was obtained.

Thus obtained preparation was used such that one sheet thereof was given as a single dose at the time of application. The blending amount of morphine per single dose in terms of base was 426 mg.

Comparative Example 10

11.9 parts by mass of morphine hydrochloride, 3.3 parts by mass of liquid paraffin, 21.6 parts by mass of propylene glycol, 10.7 parts by mass of polyethylene glycol 400, 1.5 parts by mass of crotamiton, 3.0 parts by mass of oleyl alcohol, 7.2 parts by mass of polyoxyethylene (9) lauryl ether, 0.4 parts by mass of lactic acid and 40.4 parts by mass of ethanol were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, 4.7 g of thus obtained medicinal composition for transdermal absorption was taken with a Pasteur pipette and put in a 6 cm×6 cm square bag formed of an ethylene vinyl acetate copolymer film (thickness: 40 μm, content of vinyl acetate: about 10%). The bag was heat-sealed such that a very small amount of air was left therein.

Further, on one surface of the bag, an adhesive tape in which an acrylic adhesive was laminated on a vinyl chloride film (manufactured by Kyowa Limited, Model No: AKH-HZL 641, film thickness: 60 μm, total thickness: about 100 μm) and which was cut into about 10 cm×10 cm was placed as an impermeable layer, whereby a reservoir preparation was obtained.

Thus obtained preparation was used such that one sheet thereof was given as a single dose at the time of application. The blending amount of morphine per single dose in terms of base was 426 mg.

Reference Example 1

10.0 parts by mass of morphine hydrochloride, 5.9 parts by mass of liquid paraffin, 38.5 parts by mass of propylene glycol, 19.2 parts by mass of polyethylene glycol 400, 2.5 parts by mass of crotamiton, 5.3 parts by mass of oleyl alcohol, 13.0 parts by mass of polyoxyethylene (9) lauryl ether, 0.6 parts by mass of lactic acid and 5.0 parts by mass of water were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, a medicinal composition storing unit was produced in the same manner as in Example 1, and the resulting unit was subjected to a test as a transdermal absorption preparation as it is.

Thus obtained preparation was used such that one set including two sheets thereof was given as a single dose at the time of application, and the blending amount of morphine per single dose in terms of base was 213 mg.

Reference Example 2

10.0 parts by mass of morphine hydrochloride, 5.6 parts by mass of liquid paraffin, 36.0 parts by mass of propylene glycol, 18.1 parts by mass of polyethylene glycol 400, 2.5 parts by mass of crotamiton, 5.0 parts by mass of oleyl alcohol, 12.2 parts by mass of polyoxyethylene (9) lauryl ether, 0.6 parts by mass of lactic acid and 10.0 parts by mass of water were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, thus obtained medicinal composition for transdermal absorption was treated in the same manner as in Example 1, whereby a medicinal composition storing unit was produced.

Further, thus obtained medicinal composition storing unit was treated in the same manner as in Example 1, whereby a transdermal absorption preparation was obtained.

Thus obtained preparation was used such that one set including two sheets thereof was used as a single dose at the time of application, and the blending amount of morphine per single dose in terms of base was 213 mg.

Reference Example 3

10.0 parts by mass of morphine hydrochloride, 4.9 parts by mass of liquid paraffin, 31.7 parts by mass of propylene glycol, 15.8 parts by mass of polyethylene glycol 400, 2.2 parts by mass of crotamiton, 4.3 parts by mass of oleyl alcohol, 10.6 parts by mass of polyoxyethylene (9) lauryl ether, 0.5 parts by mass of lactic acid and 20.0 parts by mass of water were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, thus obtained medicinal composition for transdermal absorption was treated in the same manner as in Example 1, whereby a medicinal composition storing unit was produced.

Further, thus obtained medicinal composition storing unit was treated in the same manner as in Example 1, whereby a transdermal absorption preparation was obtained.

Thus obtained preparation was used such that one set including two sheets thereof was used as a single dose at the time of application, and the blending amount of morphine per single dose in terms of base was 213 mg.

Reference Example 4

10.0 parts by mass of morphine hydrochloride, 4.2 parts by mass of liquid paraffin, 27.1 parts by mass of propylene glycol, 13.6 parts by mass of polyethylene glycol 400, 1.8 parts by mass of crotamiton, 3.7 parts by mass of oleyl alcohol, 9.1 parts by mass of polyoxyethylene (9) lauryl ether, 0.5 parts by mass of lactic acid and 30.0 parts by mass of water were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, thus obtained medicinal composition for transdermal absorption was treated in the same manner as in Example 1, whereby a medicinal composition storing unit was produced.

Further, thus obtained medicinal composition storing unit was treated in the same manner as in Example 1, whereby a transdermal absorption preparation was obtained.

Thus obtained preparation was used such that one set including two sheets thereof was used as a single dose at the time of application, and the blending amount of morphine per single dose in terms of base was 213 mg.

Reference Example 5

10.0 parts by mass of morphine hydrochloride, 11.5 parts by mass of liquid paraffin, 37.1 parts by mass of polyethylene glycol 400, 5.0 parts by mass of crotamiton, 10.2 parts by mass of oleyl alcohol, 25.0 parts by mass of polyoxyethylene (9) lauryl ether and 1.2 parts by mass of lactic acid were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, thus obtained medicinal composition for transdermal absorption was treated in the same manner as in Example 1, whereby a medicinal composition storing unit was produced.

Further, thus obtained medicinal composition storing unit was treated in the same manner as in Example 1, whereby a transdermal absorption preparation was obtained.

Thus obtained preparation was used such that one set including two sheets thereof was used as a single dose at the time of application, and the blending amount of morphine per single dose in terms of base was 213 mg.

Reference Example 6

10.0 parts by mass of morphine hydrochloride, 8.2 parts by mass of liquid paraffin, 52.5 parts by mass of propylene glycol, 3.6 parts by mass of crotamiton, 7.2 parts by mass of oleyl alcohol, 17.6 parts by mass of polyoxyethylene (9) lauryl ether and 0.9 parts by mass of lactic acid were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, thus obtained medicinal composition for transdermal absorption was treated in the same manner as in Example 1, whereby a medicinal composition storing unit was produced.

Further, thus obtained medicinal composition storing unit was treated in the same manner as in Example 1, whereby a transdermal absorption preparation was obtained.

Thus obtained preparation was used such that one set including two sheets thereof was used as a single dose at the time of application, and the blending amount of morphine per single dose in terms of base was 213 mg.

Reference Example 7

10.0 parts by mass of morphine hydrochloride, 43.7 parts by mass of propylene glycol, 21.8 parts by mass of polyethylene glycol 400, 3.0 parts by mass of crotamiton, 6.0 parts by mass of oleyl alcohol, 14.8 parts by mass of polyoxyethylene (9) lauryl ether and 0.7 parts by mass of lactic acid were mixed, and the resulting mixture was stirred for about 1 minute in an ultrasonic bath to uniformly disperse morphine hydrochloride, whereby a medicinal composition for transdermal absorption as a white suspension liquid was obtained.

Subsequently, thus obtained medicinal composition for transdermal absorption was treated in the same manner as in Example 1, whereby a medicinal composition storing unit was produced.

Further, thus obtained medicinal composition storing unit was treated in the same manner as in Example 1, whereby a transdermal absorption preparation was obtained.

Thus obtained preparation was used such that one set including two sheets thereof was used as a single dose at the time of application, and the blending amount of morphine per single dose in terms of base was 213 mg.

Test Example 1

Active Ingredient Availability Test

By using rabbits as experimental animals, the plasma concentration of the active ingredient after the preparation was applied was measured over time for the preparations obtained in the above-mentioned Examples, Reference examples and Comparative examples according to the following procedure. Further, the amount of the active ingredient remaining in each of the preparations after they were used in this test was measured and the residual amount of the active ingredient was determined. The results of the preparations of Examples, Comparative examples and Reference examples for these tests are shown in Table 1, Table 2 and Table 3, respectively.

(Treatment of Experimental Animals)

Male Japanese white rabbits (body weight: about 2.0 kg) were used in the experiment under nonfasting conditions. The number of animals in each group was set to 1 to 3. The rabbits were basically given a chow and water ad libitum throughout the experimental period. On the day when the transdermal absorption preparation was to be applied, the back of each rabbit was shaven with electrical clippers. At this time, attention was paid so as not to injure the skin with the electrical clippers, and the hair was shaved to a length of about 0.1 to 0.5 mm.

Thereafter, a necessary number of sheets of the transdermal absorption preparation for achieving the effective transdermal absorption area shown in each table were applied to the back of each rabbit. Then, the torso of the rabbit was wrapped in a non-woven adhesive bandage (Mesh pore tape, Nichiban Co., Ltd., Model No: 50F, 5.0 cm (width)×about 50 cm (length)) over a width of about 15 cm once or twice so as to cover and fix the preparation. The application time was set to 24 hours, 48 hours and 72 hours for each specimen. After the preparation was applied, the blood was collected over time through the ear vein.

(Collection and Treatment of Blood)

About 4 mL of blood was collected from each rabbit through the ear vein immediately before the application of the transdermal absorption preparation (0 hours) and 24, 48 and 72 hours after the application of the preparation (however, until the maximum time of application of the transdermal absorption preparation). Then, the blood was put in a tube to which heparin (40 U/40 μL (physiological saline)) was previously added, which was then transferred to a blood collection tube and cooled in ice. Then, the tube was centrifuged at 3000 rpm for 20 minutes to obtain the plasma, which was cryopreserved at −20° C. as needed until the concentration of the active ingredient was measured.

(Measurement of Plasma Concentration of Active Ingredient)

To 2 mL of the plasma, 2 mL of a 0.1 M sodium borate buffer (pH 9.5) was added and mixed with a mixer. Then, 10 mL of ethyl acetate/acetone (3:1 (v/v)) was added thereto, and the mixture was shaken at room temperature in a shaker for 10 minutes. Thereafter, the mixture was centrifuged at 3000 rpm for 10 minutes at 20° C. and the resulting supernatant organic layer was collected. Further, to the residue, 10 mL of ethyl acetate/acetone (3:1 (v/v)) was added and the mixture was shaken at room temperature in a shaker for 10 minutes. Thereafter, the mixture was centrifuged at 3000 rpm for 10 minutes at 20° C. and the resulting supernatant was collected and combined with the previously collected supernatant. Thus obtained supernatant was concentrated with an evaporator and the residue was dissolved in 0.4 mL of distilled water. The obtained solution was centrifuged at 14,800 rpm for 10 minutes at 4° C. and the resulting supernatant was subjected to high performance liquid chromatography to measure the plasma concentration of the active ingredient.

The measurement conditions for high performance liquid chromatography are as follows.

Detector: an ultraviolet absorptiometer (measurement wavelength: 215 nm)

Column: a column obtained by packing octadecylsilylated silica gel for liquid chromatography chemically modified with fluorinated silicon with a particle size of 5 μm into a stainless steel tube with an inner diameter of 4.6 mm and a length of 25 cm Column temperature: constant temperature of around 40° C.

Mobile phase: a mobile phase obtained by adding 0.5 w/v % of sodium dodecyl sulfate and 0.4 v/v % of acetic acid to water/acetonitrile (65:35)

Flow rate: the flow rate was adjusted such that the retention time of the active ingredient became about 20 minutes.

(Measurement of Residual Ratio of Active Ingredient)

Each transdermal absorption preparation after it was applied to the rabbit in Test example 1 was collected, and the part to which the medicinal composition was not adhered was cut off or removed and the remaining part was used as a test specimen. Subsequently, to this test specimen, 30 mL of methanol/hexane (1:1 (v/v)) was added and the mixture was shaken at room temperature in a shaker for 10 minutes. Then, 15 mL of water was added thereto and the mixture was shaken at room temperature in a shaker for 10 minutes. Thereafter, the mixture was centrifuged at 3000 rpm for 10 minutes at 20° C. and then, hexane was removed and the lower supernatant was collected. Further, to the residue, 20 mL of methanol/hexane (1:1 (v/v)) was added and the mixture was shaken at room temperature in a shaker for 10 minutes. Then, 10 mL of water was added thereto and the mixture was shaken at room temperature in a shaker for 10 minutes. Thereafter, the mixture was centrifuged at 3000 rpm for 10 minutes at 20° C., and then, the lower supernatant was collected and combined with the previously collected lower supernatant.

Thus obtained lower supernatant was concentrated with an evaporator and the residue was dissolved in 100 mL of distilled water. The obtained solution was filtered through a membrane filter with a pore size of 0.45 μm. The resulting filtrate was diluted and subjected to high performance liquid chromatography to measure the concentration of the active ingredient in the test specimen. The measurement conditions for high performance liquid chromatography are the same as above.

Incidentally, the preparation which was not applied to the rabbits was used as the control, and the test results were corrected by taking the residual amount of the active ingredient obtained from the control as 100% and the residual ratio was calculated. Further, from thus obtained residual ratio and the amount of the active ingredient per single dose of each preparation, the available amount of the active ingredient in the transdermal absorption preparation was calculated. The results of the preparations of Examples and Comparative examples for this test are shown in Table 1 and Table 2, respectively.

(Results)

The results of measuring the plasma concentration of the active ingredient over time after the preparation was applied and the results of measuring the residual amount of the active ingredient of the preparation after it was used in this test of the preparations of Examples, Comparative examples, and Reference examples are shown in Table 1, Table 2 and Table 3, respectively.

TABLE 1

| Preparation | Amount of active ingredient per single dose (mg) | Effective transdermal absorption area (cm$^2$) | Plasma concentration after application (ng/mL) | | | Residual ratio of active ingredient (%) | Available amount of active ingredient (mg) |
|---|---|---|---|---|---|---|---|
| | | | 24 h | 48 h | 72 h | | |
| Example 1 | 213 | 34.7 | 280 | 115 | 28 | 5 | 202.4 |
| Example 2 | 410 | 34.7 | 328 | 245 | 119 | 7 | 381.3 |
| Example 3 | 213 | 17.4 | 293 | 79 | 26 | 15 | 181.1 |
| Example 4 | 213 | 17.4 | 275 | 121 | 63 | 10 | 191.7 |
| Example 5 | 213 | 34.7 | 87 | 156 | 71 | 34 | 140.6 |
| Example 6 | 213 | 34.7 | 217 | 150 | 74 | 16 | 178.9 |
| Example 7 | 213 | 34.7 | 97 | 65 | 21 | 27 | 155.5 |
| Example 8 | 213 | 34.7 | 108 | 128 | 60 | 11 | 189.6 |
| Example 9 | 213 | 34.7 | 125 | 67 | 37 | 12 | 187.4 |
| Example 10 | 213 | 34.7 | 97 | 121 | 46 | 31 | 147 |
| Example 11 | 213 | 34.7 | 50 | 133 | 103 | 54 | 98 |
| Example 12 | 213 | 34.7 | 107 | 375 | 222 | 17 | 176.8 |
| Example 13 | 207 | 34.7 | 92 | 246 | 108 | 16 | 173.9 |

Note)
The amount of active ingredient is shown in terms of morphine base.

TABLE 2

| Preparation | Amount of active ingredient per single dose (mg) | Effective transdermal absorption area (cm²) | Plasma concentration after application (ng/mL) | | | Residual ratio of active ingredient (%) | Available amount of active ingredient (mg) |
|---|---|---|---|---|---|---|---|
| | | | 24 h | 48 h | 72 h | | |
| Comparative example 1 | 155 | 60.5 | 12 | 11 | N/A | N/A | N/A |
| Comparative example 2 | 74 | 60.5 | 17 | 2 | N/A | (37) | N/A |
| Comparative example 3 | 289 | 78.4 | 0 | N/A | N/A | (79) | N/A |
| Comparative example 4 | 166 | 60.5 | 97 | 30 | 16 | 37 | — |
| Comparative example 5 | 126 | 60.5 | 42 | 7 | 5 | 65 | 44.1 |
| Comparative example 6 | 213 | 34.7 | 0 | N/A | N/A | (100) | N/A |
| Comparative example 7 | 213 | 34.7 | 14 | 10 | 19 | 68 | 68.2 |
| Comparative example 8 | 213 | 34.7 | 11 | 55 | 31 | 40 | 127.8 |
| Comparative example 9 | 426 | 36.0 | 3 | N/A | N/A | (97) | N/A |
| Comparative example 10 | 426 | 36.0 | 0 | N/A | N/A | (107) | N/A |

Note 1)
The amount of active ingredient is shown in terms of morphine base.
Note 2)
N/A indicates that the data has not been measured.
Note 3)
The parenthesized numerical value means a residual ratio based on the measurement value of the concentration of the active ingredient in the final plasma.
Note 4)
The residual ratio of the active ingredient of Comparative example 4 has not been corrected for the control value.

TABLE 3

| Preparation | Amount of active ingredient per single dose (mg) | Effective transdermal absorption area (cm²) | Plasma concentration after 24-hour application (ng/mL) | Residual ratio of active ingredient after 24-hour application (%) |
|---|---|---|---|---|
| Reference example 1 | 213 | 34.7 | 150 | 59 |
| Reference example 2 | 213 | 34.7 | 138 | 59 |
| Reference example 3 | 213 | 34.7 | 112 | 57 |
| Reference example 4 | 213 | 34.7 | 35 | 50 |
| Reference example 5 | 213 | 34.7 | 287 | 53 |
| Reference example 6 | 213 | 34.7 | 338 | 26 |
| Reference example 7 | 213 | 34.7 | 243 | 38 |

Note)
The amount of active ingredient is shown in terms of morphine base.

From the above results, in the case of the preparation in which the base had shape retainability, i.e., the active ingredient-holding vehicle did not have fluidity as in Comparative examples 1 to 5, the plasma concentration of the active ingredient was not sufficient.

Further, in the case of the preparation in which all the transdermal absorption accelerators were omitted as in Comparative example 6, the transdermal absorption of the active ingredient was not at all observed at least at 24 hours after application.

Further, in the case of the preparation in which the active ingredient was completely dissolved as in Comparative example 7, the plasma concentration of the active ingredient was not sufficient.

Further, also in the case of the reservoir preparation in which the medicinal composition was encapsulated in an ethylene vinyl acetate copolymer film as in Comparative example 9, the plasma concentration of the active ingredient was not sufficient.

On the other hand, in the case of the preparation comprising the support having voids with which the medicinal composition for transdermal absorption in which the active ingredient was blended in such an amount as corresponding to the saturation solubility or more in the active ingredient-holding vehicle having fluidity at a temperature around the human skin surface temperature and at least a portion of the active ingredient was held in a crystalline form as in Examples 1 to 13 was carried, a sufficient plasma concentration of the active ingredient was obtained. In particular, with the preparations of Examples 2, 4, 5, 6, 8, and 10 to 13, a high plasma concentration of the active ingredient was obtained even at 72 hours after application.

Further, from the results of the preparations having a water content of from 5 to 50% (Comparative example 8 and Reference examples 1 to 4), a tendency was observed that the transdermal absorption of the active ingredient was decreased as the blending amount of water was increased (FIG. 2).

Test Example 2

Test for Determination of Ratio of Dissolved Active Ingredient

According to the following procedure, for the preparations in which it was visually confirmed that at least a portion of the active ingredient was present in a crystalline form in the medicinal composition for transdermal absorption, the ratio of the dissolved morphine to the total contained morphine was determined. That is, each of the medicinal compositions which were confirmed to have the active ingredient in a crystalline form was uniformly mixed, and a predetermined amount thereof was weighed out and placed in a centrifugal filter unit (ULTRAFREE-MC, Amicon Co., Model No: UFC30HV00, 0.45 μm filter unit) and then subjected to centrifugal filtration at 12,000 G for 5 minutes at 20° C. Thereafter, a portion of the filtrate was taken and diluted with a good solvent for the active ingredient (in the case where the active ingredient is morphine hydrochloride, the good solvent is purified water) and subjected to high performance liquid chromatography to measure the amount of the active ingredient in the filtrate. Further, the ratio of the dissolved active ingredient was calculated from this value, the amount of the active ingredient-holding vehicle and the blending amount of the active ingredient. The results are shown in Table 4. Incidentally, the measurement conditions for high performance liquid chromatography are the same as in Test example 1.
(Results)

TABLE 4

| Preparation No. | Ratio of dissolved active ingredient at 20° C. (%) |
|---|---|
| Example 1 | 23.1 |
| Example 2 | 23.1 |
| Example 3 | 5.5 |
| Example 4 | 5.5 |
| Example 5 | N/A |
| Example 6 | 0.1 |
| Example 7 | 30.4 |
| Example 8 | 20.0 |
| Example 9 | 24.3 |
| Example 10 | 23.9 |
| Example 11 | 0.0 |
| Example 12 | N/A |
| Example 13 | N/A |
| Comparative example 6 | 40.1 |
| Comparative example 8 | 43.5 |

From these results, a tendency was observed that the formulation in which the ratio of the dissolved active ingredient was high showed low transdermal absorption.

Example 14

The respective components were mixed at the ratio for each of preparations A to C shown in Table 5, and the resulting mixture was stirred for about 1 minute in an ultrasonic bath to uniformly disperse morphine hydrochloride, whereby medicinal compositions for transdermal absorption as a white suspension liquid were obtained.

Subsequently, about 0.3 g of each of thus obtained medicinal compositions for transdermal absorption was taken with a Pasteur pipette and dropped uniformly on the whole area of an open-cell polyethylene sponge foam (manufactured by Inoac Corporation, trade name: MAPS, Model No: ST-15, cell size: about 55 μm, void ratio: about 85%, thickness: about 1 mm) which had been fixed by melting on an aluminum deposited film (manufactured by Mitsubishi Plastics, Inc., PE (12 μm)/PET (15 μm)/Al (9 μm)/PE (30 μm)) by heat sealing such that it became a square with a side length of about 22 mm, whereby a medicinal composition storing unit integrated with an impermeable layer was produced.

Further, on the surface of the impermeable layer side of thus obtained medicinal composition storing unit integrated with an impermeable layer, a polyurethane film (manufactured by Kyowa Limited, Million Aid Dressing Tape, Model No: MA-E150-A, thickness: 30 μm) which was cut into about 10 cm×10 cm was placed as an adhesive layer and an adhesive holding layer, whereby a transdermal absorption preparation was obtained.

Thus obtained preparation was used such that one sheet thereof was given as a single dose at the time of application, and the blending amount of the active ingredient per single dose in terms of base was 45.6 mg.

Test Example 3

Active Ingredient Availability Test (Hairless Rats)

By using hairless rats as experimental animals, the plasma concentration of the active ingredient after the preparation was applied was measured over time for the preparations obtained in Example 14 according to the following procedure.
(Treatment of Experimental Animals)

Male hairless rats (body weight: about 200 g) were used in the experiment under nonfasting conditions. The number of animals in each group was set to 3. The hairless rats were basically given a chow and water ad libitum throughout the experimental period. On the day when the transdermal absorption preparation was to be applied, the abdominal area of each rat was wiped with a non-woven cloth containing water and dried, and then, the rat was subjected to the experiment.

Thereafter, one sheet of the transdermal absorption preparation was applied to the abdominal area of the hairless rat. Then, the torso of the hairless rat was wrapped in a non-woven adhesive bandage (Mesh pore tape, Nichiban Co., Ltd., Model No: 50F, 5.0 cm (width)×about 20 cm (length)) over a width of about 15 cm once or twice so as to cover and fix the preparation. The application time was set to 24 hours and 48 hours for each specimen. After the preparation was applied, the blood was collected over time through the jugular vein.
(Collection and Treatment of Blood)

About 2 mL of blood was collected from each hairless rat through the jugular vein immediately before the application of the transdermal absorption preparation (0 hours) and 24 and 48 hours after the application of the preparation. Then, the blood was put in a tube to which heparin (40 U/40 μL (physiological saline)) was previously added, which was then transferred to a blood collection tube and cooled in ice. Then, the tube was centrifuged at 3000 rpm for 20 minutes to obtain the plasma, which was cryopreserved at −20° C. as needed until the concentration of the active ingredient was measured.
(Measurement of Plasma Concentration of Active Ingredient)

To 1 mL of the plasma, 3 mL of a 0.5 M ammonia buffer (pH 9.3) and 0.2 mL of a 0.1 M pentane sulfonate buffer were added and mixed with a mixer. Then, the resulting mixture was added to a solid-phase extraction cartridge (manufactured by Varian Inc., Bond Elut C18) conditioned with 2 mL of methanol and 2 mL of a 0.5 M ammonia buffer (pH 9.3). Then, the cartridge was washed by sequentially adding 10 mL of a 5 mM ammonia buffer (pH 9.3) and 0.5 mL of distilled water. The cartridge was dried under reduced pressure and then eluted with 3 mL of methanol. The eluate was concentrated with an evaporator and the residue was dissolved in 0.4 mL of distilled water. The obtained solution was filtered through a membrane filter (manufactured by Millipore Corporation, trade name: Millex LH, pore size: 0.45 μm). The filtrate was subjected to high performance liquid chromatography to measure the plasma concentration of the active ingredient.

The conditions for measuring the plasma drug concentration by high performance liquid chromatography are as follows.

Detector: an electrochemical detector (voltage: 0.6 V, sensitivity: 0.1)

Column: a column obtained by packing octadecylsilylated silica gel for liquid chromatography chemically modified with fluorinated silicon with a particle size of 5 µm into a stainless steel tube with an inner diameter of 3.0 mm and a length of 15 cm Column temperature: constant temperature of around 35° C.

Mobile phase: 50 mM ammonium acetate solution/acetonitrile (9:1)

Flow rate: the flow rate was adjusted such that the retention time of the active ingredient became about 20 minutes.

(Results)

The results of measuring the plasma concentration of the active ingredient after the preparation was applied are shown in Table 5.

Example 15

The respective components were mixed at the ratio for a preparation B shown in Table 5, and the resulting mixture was stirred for about 1 minute in an ultrasonic bath to uniformly disperse morphine hydrochloride, whereby a medicinal composition for transdermal absorption as a white suspension liquid was obtained.

Subsequently, about 3.0 g of thus obtained medicinal composition for transdermal absorption was taken with a Pasteur pipette and dropped uniformly on the whole area of an open-cell polyethylene sponge foam (manufactured by Inoac Corporation, trade name: MAPS, Model No: ST-15, cell size: about 55 µm, void ratio: about 85%, thickness: about 1 mm) which had been fixed by melting on an aluminum deposited film (manufactured by Mitsubishi Plastics, Inc., PE (12 µm)/PET (15 µm)/Al (9 µm)/PE (30 µm)) by heat sealing such that it became a square with a side length of about 55 mm, whereby a medicinal composition storing unit integrated with an impermeable layer was produced.

Further, on the surface of the impermeable layer side of thus obtained medicinal composition storing unit integrated with an impermeable layer, a polyurethane film (manufactured by Kyowa Limited, Million Aid Dressing Tape, Model No: MA-E150-A, thickness: 30 µm) which was cut into about 10 cm×10 cm was placed as an adhesive layer and an adhesive holding layer, whereby a transdermal absorption preparation was obtained.

Thus obtained preparation was used such that one sheet thereof was given as a single dose at the time of application, and the blending amount of the active ingredient per single dose in terms of base was 455.5 mg.

Test Example 4

Active Ingredient Availability Test (Miniature Pigs)

By using miniature pigs as experimental animals, the plasma concentration of the active ingredient after the preparation was applied was measured over time for the preparation obtained in the above Example according to the following procedure.

(Treatment of Experimental Animals)

Male miniature pigs (NIBS) (body weight: about 23 kg) were used in the experiment under nonfasting conditions. The number of the animals was set to 4. The miniature pigs were basically given a chow and water ad libitum throughout the experimental period. On the day before when the transdermal absorption preparation was to be applied, the back of each miniature pig was shaven with electrical clippers. At this time, attention was paid so as not to injure the skin with the electrical clippers. On the experimental day, the intended application site was washed with a medicinal soap and dried, and then, the pig was subjected to the experiment.

Thereafter, one sheet of the transdermal absorption preparation was applied to the back of the miniature pig. Then, the torso of the miniature pig was wrapped in a non-woven adhesive bandage (Mesh pore tape, Nichiban Co., Ltd., Model No: 50F, 5.0 cm (width)×about 30 cm (length)) over a width of about 15 cm once or twice so as to cover and fix the preparation. The application time was set to 24 hours or more. After the preparation was applied, the blood was collected over time.

(Collection and Treatment of Blood)

About 6 mL of blood was collected from each miniature pig through the jugular sinus of the vena cava immediately before the application of the transdermal absorption preparation (0 hours) and 8 and 24 hours after the application of the preparation. Then, the blood was put in a tube to which heparin (40 U/40 µL (physiological saline)) was previously added, which was then transferred to a blood collection tube and cooled in ice. Then, the tube was centrifuged at 3000 rpm for 20 minutes to obtain the plasma, which was cryopreserved at −20° C. as needed until the concentration of the active ingredient was measured.

(Measurement of Plasma Concentration of Active Ingredient)

The filtrate obtained by the same procedure as in the active ingredient availability test using the hairless rats was subjected to high performance liquid chromatography to measure the plasma concentration of the active ingredient.

The conditions for measuring the plasma drug concentration by high performance liquid chromatography are also the same as in the active ingredient availability test using the hairless rats.

(Results)

The results of measuring the plasma concentration of the active ingredient after the preparation was applied are shown in Table 5.

Test Example 5

Human Skin Irritation Test

A medicinal composition storing unit prepared in the same manner as in Example 14 (however, morphine hydrochloride was not contained and the impermeable layer was not used) was placed on the skin on the inner side of the upper arm or the lower arm of each of three healthy male adults and a polyurethane film (manufactured by Kyowa Limited, Million Aid Dressing Tape, Model No: MA-E150-A, thickness: 30 µm) which was cut into about 10 cm×10 cm was applied thereto to cover the unit and fixed thereon. Then, the test subjects were allowed to perform normal daily activities for 48 hours while applying the unit. 48 hours after the application, the condition of the skin where the medicinal composition storing unit was placed was observed and also the skin sensation of the test subjects during application thereof was examined. The test results are shown in Table 5.

TABLE 5

|  | Preparation A | Preparation B | Preparation C |
|---|---|---|---|
| Morphine hydrochloride | 2.0 | 2.0 | 2.0 |
| Propylene glycol | 0.5 | 1.5 | 2.5 |
| Concentrated glycerin | 5.5 | 4.0 | 2.0 |
| Polyoxyethylene (9) lauryl ether | 0.5 | 1.0 | 2.0 |
| Butylhydroxyanisol | 0.02 | 0.02 | 0.02 |
| Ascorbic acid | 0.01 | 0.01 | 0.01 |
| 1,3-butylene glycol | 0.5 | 0.5 | 0.5 |
| Water | 0.97 | 0.97 | 0.97 |
| Total | 10.0 | 10.0 | 10.0 |
| Human skin irritation test | slight reddening and no itching | slight reddening and slight itching | heavy reddening and heavy itching |
| Plasma concentration 24 hours after application in hairless rats (ng/mL) | 64.9 | 197.6 | 201.4 |
| Plasma concentration 48 hours after application in hairless rats (ng/mL) | 133.0 | 166.1 | 156.9 |
| Plasma concentration 24 hours after application in miniature pigs (ng/mL) | — | 48.8 | — |

Note)
The test was discontinued for one subject 24 hours after application of the preparation C in the human skin irritation test due to itching.

From the above results, it was found that all the preparations A to C showed good transdermal absorption in plural animal species and the effects of the preparations were closely associated with the concentrations of propylene glycol, 1,3-butylene glycol, polyoxyethylene lauryl ether and glycerin. Further, in comparison between the preparations B and C, it was found that even if the concentrations of the above components were increased, the effect in increasing the transdermal absorption reached a ceiling and only the skin irritation was increased.

Example 16

The respective components were mixed at the ratio shown in Table 6, and the resulting mixture was stirred for about 1 minute in an ultrasonic bath to uniformly disperse morphine hydrochloride, whereby a medicinal composition for transdermal absorption as a white suspension liquid was obtained.

Subsequently, about 3.0 g of thus obtained medicinal composition for transdermal absorption was taken with a Pasteur pipette and dropped uniformly on the whole area of an open-cell polyethylene sponge foam (manufactured by Inoac Corporation, trade name: MAPS, Model No: ST-15, cell size: about 55 µm, void ratio: about 85%, thickness: about 1 mm) which had been fixed by melting on an aluminum deposited film (manufactured by Mitsubishi Plastics, Inc., PE (12 µm)/PET (15 µm)/Al (9 µm)/PE (30 µm)) by heat sealing such that it became a square with a side length of about 5.5 mm, whereby a medicinal composition storing unit integrated with an impermeable layer was produced.

Further, on the surface of the impermeable layer side of thus obtained medicinal composition storing unit integrated with an impermeable layer, a polyurethane film (manufactured by Kyowa Limited, Million Aid Dressing Tape, Model No: MA-E150-A, thickness: 30 µm) which was cut into about 10 cm×10 cm was placed as an adhesive layer and an adhesive holding layer, whereby a transdermal absorption preparation was obtained.

Thus obtained preparation was used such that two sheets thereof were given as a single dose at the time of application, and the blending amount of the active ingredient per single dose in terms of base was 911.0 mg.

Test Example 6

Active Ingredient Availability Test (Miniature Pig)

By using a miniature pig as an experimental animal, the plasma concentration of the active ingredient after the preparation was applied was measured over time for the preparation obtained in the above Example.
(Treatment of Experimental Animal)

A male miniature pig (NIBS) (body weight: about 23 kg) was used in the experiment under nonfasting conditions. The number of animals was set to 1. The miniature pig was basically given a chow and water ad libitum throughout the experimental period. On the day before when the transdermal absorption preparation was to be applied, the back of the miniature pig was shaven with electrical clippers. At this time, attention was paid so as not to injure the skin with the electrical clippers. On the experimental day, the intended application site was washed with a medicinal soap and dried, and then, the pig was subjected to the experiment.

Thereafter, two sheets of the transdermal absorption preparation were applied to the back of the miniature pig. Then, the torso of the miniature pig was wrapped in a non-woven adhesive bandage (Mesh pore tape, Nichiban Co., Ltd., Model No: 50F, 5.0 cm (width)×about 30 cm (length)) over a width of about 15 cm once or twice so as to cover and fix the preparation. The application time was set to 48 hours. After the preparation was applied, the blood was collected over time.
(Collection and Treatment of Blood)

About 6 mL of blood was collected from the miniature pig through the jugular sinus of the vena cava immediately before the application of the transdermal absorption preparation (0 hours) and 24 and 48 hours after the application of the preparation. Then, the blood was put in a tube to which heparin (40 U/40 µl, (physiological saline)) was previously added, which was then transferred to a blood collection tube and cooled in ice. Then, the tube was centrifuged at 3000 rpm for 20 minutes to obtain the plasma, which was cryopreserved at −20° C. as needed until the concentration of the active ingredient was measured.
(Measurement of Plasma Concentration of Active Ingredient)

The plasma concentration of the active ingredient was measured in the same manner as in Test example 4. The conditions for measuring the plasma drug concentration by high performance liquid chromatography are also the same as in Test example 4.

(Results)

The results of measuring the plasma concentration of the active ingredient after the preparation was applied are shown in Table 6.

TABLE 6

|  | Example 16 |
|---|---|
| Morphine hydrochloride | 2.0 |
| Propylene glycol | 2.0 |
| Polyethylene glycol 400 | 3.5 |
| Oleyl alcohol | 1.0 |
| Polyoxyethylene (4.2) lauryl ether | 1.5 |
| Total | 10.0 |
| Plasma concentration 24 hours after application (ng/mL) | 41.4 |
| Plasma concentration 48 hours after application (ng/mL) | 48.9 |

From the above results, it is found that the formulation shown in Table 6 also provides good sustained absorption.

INDUSTRIAL APPLICABILITY

According to the invention, it has become possible to provide a sustained release transdermal absorption preparation of morphine or a salt thereof which had not been achieved by anyone although several attempts were made worldwide in the past. This is an innovative preparation which significantly improves patients' QOL in the world who suffer from pain, particularly cancer pain and can be widely used in the field of clinical medicine.

BRIEF DESCRIPTION OF THE DRAWINGS

FIG. 2 is a graph showing a relationship between an amount of water contained in a preparation and a plasma morphine concentration after 24-hour application of the preparation.

DESCRIPTION OF REFERENCE NUMERALS AND SIGNS

Figure 1:
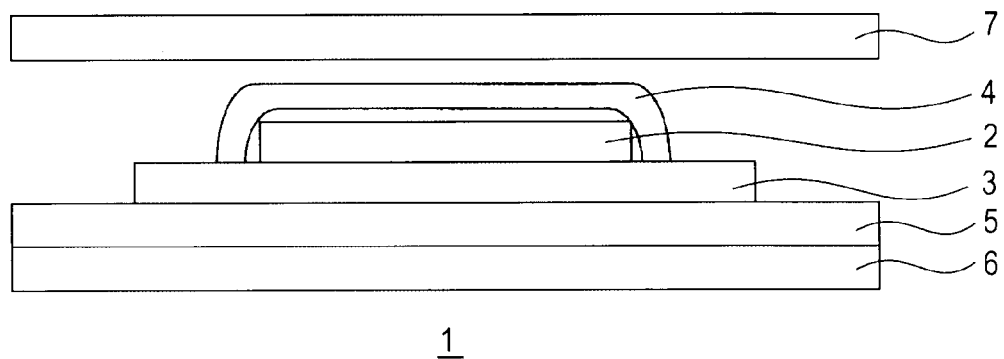
FIG. 1 is a view schematically showing a transdermal absorption preparation according to an embodiment of the invention.

1: Transdermal absorption preparation
2: Medicinal composition storing unit
3: Impermeable layer
4: Drug protecting layer
5: Adhesive layer
6: Adhesive holding layer
7: Release film

The invention claimed is:

1. A medicinal composition storing unit, comprising:
a support comprising at least one member selected from the group consisting of a compressed body of a fibrous substance, a compressed body of a powdery substance, and a sponge foam; and
a medicinal composition carried in voids within the support;
wherein:
the medicinal composition comprises an active ingredient and an active ingredient-holding vehicle;
a water content of the medicinal composition is less than 50% by mass;
the active ingredient comprises at least one of morphine and salts thereof;
the active ingredient-holding vehicle has fluidity at a temperature around human skin surface temperature;
the active ingredient-holding vehicle comprises at least one member selected from the group consisting of liquid paraffin, propylene glycol, 1,3-butylene glycol, polyethylene glycol, polyvinylpyrrolidone, a silicone oil, ceramide, cholesterol, isopropyl palmitate, lauric acid, palmitic acid, oleic acid, oleyl alcohol, polyoxyethylene lauryl ether, crotamiton, lactic acid, and water;
the active ingredient-holding vehicle further comprises at least one transdermal absorption accelerator selected from the group consisting of a saturated higher fatty acid, an unsaturated higher fatty acid, a higher alcohol, an alkylene oxide adduct of a higher alcohol, a crotonotoluidine derivative, and a hydroxy acid;
the active ingredient is blended in the active ingredient-holding vehicle in an amount corresponding to saturation solubility or greater;
at least one portion of the active ingredient is in a crystalline form;
the active ingredient-holding vehicle can move in the support; and
when a preparation comprising the medicinal composition is applied for 72 hours to uninjured skin of a back of a white rabbit having been shaved with electrical clippers:
an available amount of the active ingredient per single dose of the preparation is from 10 mg to 400 mg in terms of morphine base; and
plasma concentrations of the active ingredient 24 hours and 48 hours after application of the preparation are each at least 40 ng/mL in terms of morphine base.

2. The medicinal composition storing unit according to claim 1, wherein the active ingredient comprises at least one salt of morphine.

3. The medicinal composition storing unit according to claim 1, wherein the active ingredient comprises at least one member selected from the group consisting of morphine hydrochloride, morphine sulfate, morphine gluconate, morphine tartrate, morphine lactate, morphine methane sulphonate, and morphine phosphate.

4. The medicinal composition storing unit according to claim 1, wherein at least 30% by mass of the active ingredient is in a crystalline form.

5. The medicinal composition storing unit according to claim 1, wherein the transdermal absorption accelerator comprises at least one compound selected from the group consisting of lauric acid, palmitic acid, oleic acid, oleyl alcohol, polyoxyethylene lauryl ether, crotamiton, and lactic acid.

6. The medicinal composition storing unit according to claim 1, wherein the compressed body of a fibrous substance is a flat plate formed of a cellulose fiber.

7. The medicinal composition storing unit according to claim 1, wherein the sponge foam has an open-cell structure.

8. The medicinal composition storing unit according to claim 1, wherein the sponge foam comprises at least one material selected from the group consisting of a plastic and a rubber.

9. The medicinal composition storing unit according to claim 8, wherein:
the sponge foam comprises the plastic; and
the plastic comprises at least one compound selected from the group consisting of polyethylene, polypropylene, polyurethane, polyethylene terephthalate, and polyvinyl acetate.

10. The medicinal composition storing unit according to claim 1, wherein the medicinal composition storing unit holds a single dose of from 0.1 g to 10 g of the medicinal composition.

11. The medicinal composition storing unit according to claim 1, wherein:
the medicinal composition storing unit has an application surface for administering a single dose of the medicinal composition; and
an area of the application surface is from 3 cm$^2$ to 100 cm$^2$.

12. The medicinal composition storing unit according to claim 1, wherein the support includes voids in a void ratio of from 50% to 95%.

13. The medicinal composition storing unit according to claim 1, wherein the at least one portion of the active ingredient in the crystalline form is localized in an interior of the support or at a surface of the support.

14. The medicinal composition storing unit according to claim 13, wherein the at least one portion of the active ingredient in the crystalline form is localized at the surface of the support.

15. A transdermal absorption preparation, comprising:
the medicinal composition storing unit according to claim 1; and
sequentially laminated on a surface of the medicinal composition storing unit opposite from an application surface:
an impermeable layer that effectively prevents the active ingredient and the active ingredient-holding vehicle from permeating therethrough;
an adhesive layer; and
an adhesive holding layer.

16. The transdermal absorption preparation according to claim 15, further comprising a drug protecting layer, wherein:
the drug protecting layer has liquid permeability; and
the drug protecting layer is provided on the application surface of the medicinal composition storing unit.

17. The transdermal absorption preparation according to claim 16, wherein the drug protecting layer comprises a porous plastic film.

18. The transdermal absorption preparation according to claim 16, wherein the drug protecting layer comprises at least one material selected from the group consisting of cellulose, cellulose acetate, and nitrocellulose.

19. The transdermal absorption preparation according to claim 15, further comprising a release film, wherein:
the release film is provided at the application surface of the medicinal composition storing unit.

20. A medicinal composition storing unit, comprising:
a support comprising at least one member selected from the group consisting of a compressed body of a fibrous substance, a compressed body of a powdery substance, and a sponge foam; and
a medicinal composition carried in voids within the support;
wherein:
the medicinal composition comprises:
(A) at least one of morphine and salts thereof;
(B) at least one compound selected from the group consisting of liquid paraffin, propylene glycol, 1,3-butylene glycol, polyethylene glycol, polyvinylpyrrolidone, a silicone oil, ceramide, cholesterol, and isopropyl palmitate; and
(C) at least one compound selected from the group consisting of lauric acid, palmitic acid, oleic acid, oleyl alcohol, polyoxyethylene lauryl ether, crotamiton, and lactic acid;
a water content of the medicinal composition is less than 50% by mass;
the medicinal composition has fluidity; and
components (B) and (C) of the medicinal composition can move in the support.

21. The medicinal composition storing unit according to claim 20, wherein:
the at least one compound (B) comprises at least one of propylene glycol and 1,3-butylene glycol; and
the at least one compound (C) comprises polyoxyethylene lauryl ether.

22. The medicinal composition storing unit according to claim 21, wherein:
the at least one compound (B) is present in the medicinal composition in an amount of from 10 to 20% by mass; and
the at least one compound (C) is present in the medicinal composition in an amount of from 5 to 10% by mass.

23. The medicinal composition storing unit according to claim 21, further comprising at least one of glycerin and water.

24. The medicinal composition storing unit according to claim 20, wherein:
the at least one compound (B) comprises at least one of propylene glycol and polyethylene glycol; and
the at least one compound (C) comprises at least one of oleyl alcohol and polyoxyethylene lauryl ether.

25. The medicinal composition storing unit according to claim 24, wherein:
the at least one compound (B) is present in the medicinal composition in an amount of from 50 to 60% by mass; and
the at least one compound (C) is present in the medicinal composition in an amount of from 20 to 30% by mass.

26. A transdermal absorption preparation, comprising:
the medicinal composition storing unit according to claim 20; and
sequentially laminated on a surface of the medicinal composition storing unit opposite from an application surface:
an impermeable layer that effectively prevents the medicinal composition from permeating therethrough;
an adhesive layer; and
an adhesive holding layer.

27. A method for relieving pain, comprising applying the medicinal composition storing unit according to claim 1 to a patient with pain.

28. The medicinal composition storing unit according to claim 1, wherein the active ingredient-holding vehicle is in contact with the skin surface.

29. The medicinal composition storing unit according to claim 1, which is prepared by dropping the medicinal composition onto the support or injecting the medicinal composition into the support.

30. The medicinal composition storing unit according to claim 20, wherein components (B) and (C) of the medicinal composition are in contact with the skin surface.

31. The medicinal composition storing unit according to claim 20, which is prepared by dropping the medicinal composition onto the support or injecting the medicinal composition into the support.

* * * * *